(12) United States Patent
Candau-Chacon

US009133490B2

(10) Patent No.: US 9,133,490 B2
(45) Date of Patent: Sep. 15, 2015

(54) STEP-UP METHOD FOR COLD-PCR ENRICHMENT

(71) Applicant: Transgenomic, Inc., Omaha, NE (US)

(72) Inventor: Reyes Candau-Chacon, Olney, MD (US)

(73) Assignee: Transgenomic, Inc., Omaha, NE (US)

( * ) Notice: Subject to any disclaimer, the term of this patent is extended or adjusted under 35 U.S.C. 154(b) by 0 days.

(21) Appl. No.: 13/834,167

(22) Filed: Mar. 15, 2013

(65) Prior Publication Data

US 2013/0309724 A1 Nov. 21, 2013

Related U.S. Application Data

(60) Provisional application No. 61/647,970, filed on May 16, 2012.

(51) Int. Cl.
  *C12P 19/34* (2006.01)
  *C12Q 1/68* (2006.01)
(52) U.S. Cl.
  CPC .................. *C12P 19/34* (2013.01); *C12Q 1/686* (2013.01); *C12Q 1/6848* (2013.01)
(58) Field of Classification Search
  CPC ........................................................ C12P 19/34
  USPC ........................................................ 435/91.2
  See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,800,159 A | 1/1989 | Mullis et al. | |
| 5,045,450 A | 9/1991 | Thilly et al. | |
| 5,075,217 A | 12/1991 | Weber | |
| 5,399,491 A | 3/1995 | Kacian et al. | |
| 5,409,818 A | 4/1995 | Davey et al. | |
| 5,427,930 A | 6/1995 | Birkenmeyer | |
| 5,541,308 A * | 7/1996 | Hogan et al. | 536/23.1 |
| 5,554,527 A | 9/1996 | Fickenscher | |
| 5,565,340 A | 10/1996 | Chenchik et al. | |
| 5,612,473 A | 3/1997 | Wu et al. | |
| 5,618,703 A | 4/1997 | Gelfand et al. | |
| 5,631,147 A | 5/1997 | Lohman et al. | |
| 5,648,211 A | 7/1997 | Fraiser et al. | |
| 5,744,311 A | 4/1998 | Fraiser et al. | |
| 5,792,607 A | 8/1998 | Backman et al. | |
| 5,846,710 A | 12/1998 | Bajaj | |
| 5,849,497 A | 12/1998 | Steinman | |
| 5,994,056 A | 11/1999 | Higuichi | |
| 6,030,115 A | 2/2000 | Ishiguro et al. | |
| 6,174,680 B1 | 1/2001 | Makrigiorgos | |
| 6,197,499 B1 | 3/2001 | Hughes | |
| 7,618,773 B2 | 11/2009 | Rand et al. | |
| 8,071,338 B2 | 12/2011 | Newton | |
| 8,455,190 B2 | 6/2013 | Makrigiorgos | |
| 8,623,603 B2 | 1/2014 | Makrigiorgos | |
| 8,628,924 B2 * | 1/2014 | Kacian et al. | 435/6.12 |
| 2002/0016680 A1 | 2/2002 | Wang et al. | |
| 2003/0008286 A1 | 1/2003 | Zou et al. | |
| 2006/0063175 A1 | 3/2006 | Xu et al. | |
| 2007/0020672 A1 | 1/2007 | Wittwer et al. | |
| 2007/0154892 A1 | 7/2007 | Wain-Hobson et al. | |
| 2010/0203532 A1 | 8/2010 | Makrigiorgos | |
| 2010/0233683 A1 | 9/2010 | Molloy et al. | |
| 2011/0217714 A1 | 9/2011 | Makrigiorgos | |
| 2013/0309724 A1 | 11/2013 | Candau-Cachon | |

FOREIGN PATENT DOCUMENTS

| | | |
|---|---|---|
| EP | 0370719 | 5/1990 |
| EP | 2004852 | 12/2010 |
| GB | 2 293 238 | 3/1996 |
| JP | 2005-518216 | 6/2005 |
| WO | WO 90/11369 | 10/1990 |
| WO | WO 90/13668 | 11/1990 |
| WO | WO 91/14003 | 9/1991 |
| WO | WO 97/19193 | 5/1997 |
| WO | WO 99/14226 | 3/1999 |
| WO | WO 99/61661 | 12/1999 |
| WO | WO 01/68900 | 9/2001 |
| WO | WO 2011/112534 | 9/2001 |
| WO | WO 02/18659 | 3/2002 |
| WO | WO 03/072809 | 4/2003 |
| WO | WO 2005/093101 | 10/2005 |

(Continued)

OTHER PUBLICATIONS

Amicarelli, G. et al., "FLAG assay as a novel method for real-time signal generation during PCR: Application to detection and genotyping of KRAS codon 12 mutations," (2007) Nucleic Acids Research 35(19):e131; http://www.ncbi.nlm.nih.gov/pubmed/17932053.
Candau, R. et al., Poster Presentation: "Very High Sensitivity Detection of K-RAS Exon 2 Mutations Using Fast COLD-PCR," presented at AACR (2010).
Castellanos-Rizaldos, E. et al., "Temperature-tolerant COLD-PCR eliminates temperature stringency and enables robust mutation enrichment," (2012) Clinical Chemistry 58(7):1130-1138.
Coutelle, C., "New DNA-Analysis techniques (Minireview)," (1991) Biomed Ciochm. Acta 50(1):3-10.
Dabritz, J. et al., "Detection of Ki-ras mutations in tissue and plasma samples of patients with pancreatic cancer using PNA-mediated PCR clamping and hybridisation probes,"(2005) British Journal of Cancer 92:405-412.

(Continued)

*Primary Examiner* — Ardin Marschel
(74) *Attorney, Agent, or Firm* — Schwegman Lundberg & Woessner, P.A.

(57) ABSTRACT

Methods of using polymerase chain reactions to enrich a target sequence in a sample containing reference sequences and target sequences having high homology and amplifiable by the same primer pair are provided herein. In particular the methods provide a robust means to improve the fold enrichment of the target sequence and minimize reaction-to-reaction, well-to-well and run-to-run variations in the enrichment methods.

28 Claims, 16 Drawing Sheets

(56) References Cited

FOREIGN PATENT DOCUMENTS

| WO | WO 2007/106534 | 9/2007 |
|---|---|---|
| WO | WO 2009/017784 | 2/2009 |
| WO | WO 2009/019008 | 2/2009 |
| WO | WO 2012/135664 | 10/2012 |

OTHER PUBLICATIONS

Dominguez, P.L. et al., "Wild-type blocking polymerase chain reaction for detection of single nucleotide minority mutations from clinical specimens," Oncogene (2005) 24:6830-6834.

Frommer, et al., "A genomic sequencing protocol that yields a positive display of 5-methylcytosine residues in individual DNA strands," (1992) PNAS 89:1827.

Giesendorf, et al., "Molecular beacons: a new approch for semiautomated mutation analysis," (1998) Clinical Chemistry 44(3):482.

Jeffreys, et al., "DNA enrichment by allele-specific hybridization (DEASH): a novel method for haplotyping and for detecting low-frequency base substitutional variants and recombinant DNA molecules," (2003) Genome Research 13:1216.

Li, J. et al., "Replacing PCR with COLD-PCR enriches variant DNA sequences and redefines the sensitivity of genetic testing," Nat Med. 2008 14(5): pp. 579-584.

Li, J, et al., "Coamplification at lower denaturation temperature-PCR increases mutation-detection selectivity of TaqMan-base real-time PCT." Clinical Chemistry (2009) 55(4):748-756.

Li, J, et al., "Two-round coamplification at lower denaturation temperature-PCR (COLD-PCR)-based Sanger sequencing identifies a novel spectrum of low-level mutations in lung adenocarcinoma," (2009) Hum. Mutat. 30:1583-1590.

Li, J. et al., "COLD-PCR: A new platform for highly improved mutation detection in cancer and genetic testing," Biochemical Society Transactions, Portland Press Ltd., GB (2009) 37(2):427-432.

Li-Sucholeiki, et al., "A sensitive scanning technology for low frequency nuclear point mutations in human genomic DNA," (2000) Nucleic Acids Research 28(9):e44.

Liu, et al., "Denaturing high performance liquid chromatagraphy (DHPLC) used in the detection of germline and somatic mutations," (1998) Nucleic Acids Research 26(6):1396.

Liu, W. H., "Detection of Hotspot Mutations and Polymorphisms Using an Enhanced PCR-RFLP Approach, Human Mutation," vol. 21, Dec. 4, 2002, pp. 535-541.

Luo, J-D. et al., "Detection of rare mutant K-ras DNA in a single-tube reaction using peptide nucleic acid as both PCR clamp and sensor probe," (2006) Nucleic Acids Research, 34(2)e12, pp. 1-7.

Luthra, R. et al., "COLD-PCR finds hot application in mutation analysis," (2009) Clinical Chemistry 55(12):2077-2078.

Makrigiorgos, G.M. "PCR-based detection of minority point mutations," (2004) Human Mutations 23:406.

Milbury, C. A. et al., "PCR-based methods for the enrichment of minority alleles and mutations," (2009) Clinical Chemistry 55(4):632-640.

Milbury, C.A. et al., "COLD-PCR-enhanced high-resolution melting enables rapid and selective identification of low-level unknown mutations," (2009) Clinical Chemistry 55(12):2130-2143.

Milbury, C.A. et al., "Ice-COLD-PCR enables rapid amplification and robust enrichment for low-abundance unknown DNA mutations," Nucleic Acids Research (2011) 39(1), E2:1-10.

Oldenburg, R. P. et al., "Selective amplification of rare mutations using locked nucleic acid oligonucleotides that competitively inhibit primer binding to wild-type DNA," (2008) J. of Investigative Dermatology 128:398-402.

Orita, et al., "Rapid and sensitive detection of point mutations and DNA polymorphisms using the polymerase chain reaction," (1989) Genomics 5:874-879.

Persson, et al., "Four-color multiplex reverse transcription polymerase chain reaction—Overcoming its limitations," (2005) Analytical Biochemistry 344:33.

Sanchez, et al., "Two-temperature LATE-PCR endpoint genotyping," (2006) BMC Biotechnology 6(44) (14 pages).

Till, et al., "High-throughput discovery of rare human nucleotide polymorphisms by EcoTILLING," (2006) Nucleic Acids Research 34(13):e99.

Vestheim, H. et al., "Blocking primers to enhance PCR amplification of rare sequences in mixed samples—a case study on prey DNA in Antarctic krill stomachs," (2008) Frontiers in Zoology 5(12):1-11.

International Search Report and Written Opinion for International Patent Application No. PCT/EP2008/006476 (5 pages).

International Search Report and Written Opinion for International Patent Application No. PCT/US2011/027473 dated Jun. 28, 2011 (13 pages).

International Search Report and Written Opinion for International Patent Application No. PCT/US2008/009248 dated Jan. 6, 2009 (13 pages).

"International Application Serial No. PCT/EP2008/006476, International Search Report mailed Nov. 27, 2008", 3 pgs.

"International Application Serial No. PCT/EP2008/006476, Written Opinion mailed Nov. 27, 2008", 5 pgs.

US 7,226,736, 06/2007, Wittwer et al. (withdrawn)

\* cited by examiner

FIGURE 1

PRIOR ART

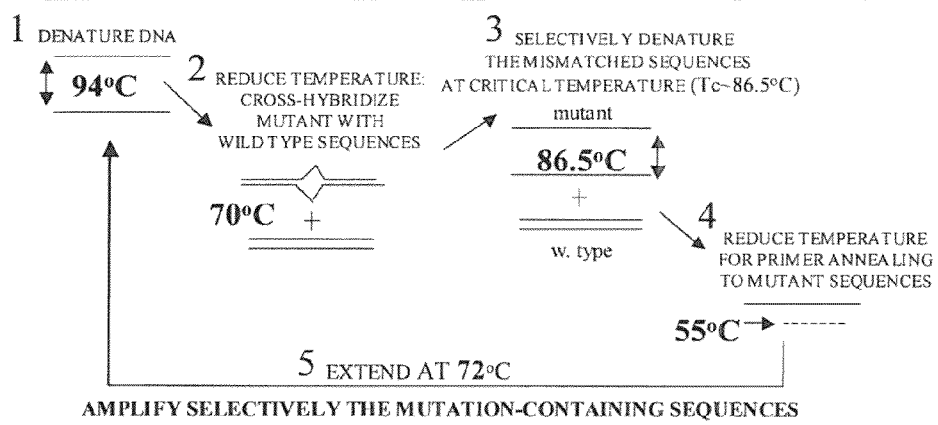

Figure 1. A. Illustration of the enrichment protocol. An example for a 167 bp p53 exon 8 sequence is depicted. The formation of mismatches anywhere along the sequence during PCR enables preferential denaturation and amplification of minor (mutant) alleles at every PCR cycle. B. Replacement of PCR with the enrichment method: All PCR-based genetic testing assays stand to benefit by mutation-enrichment during the PCR step that precedes them.

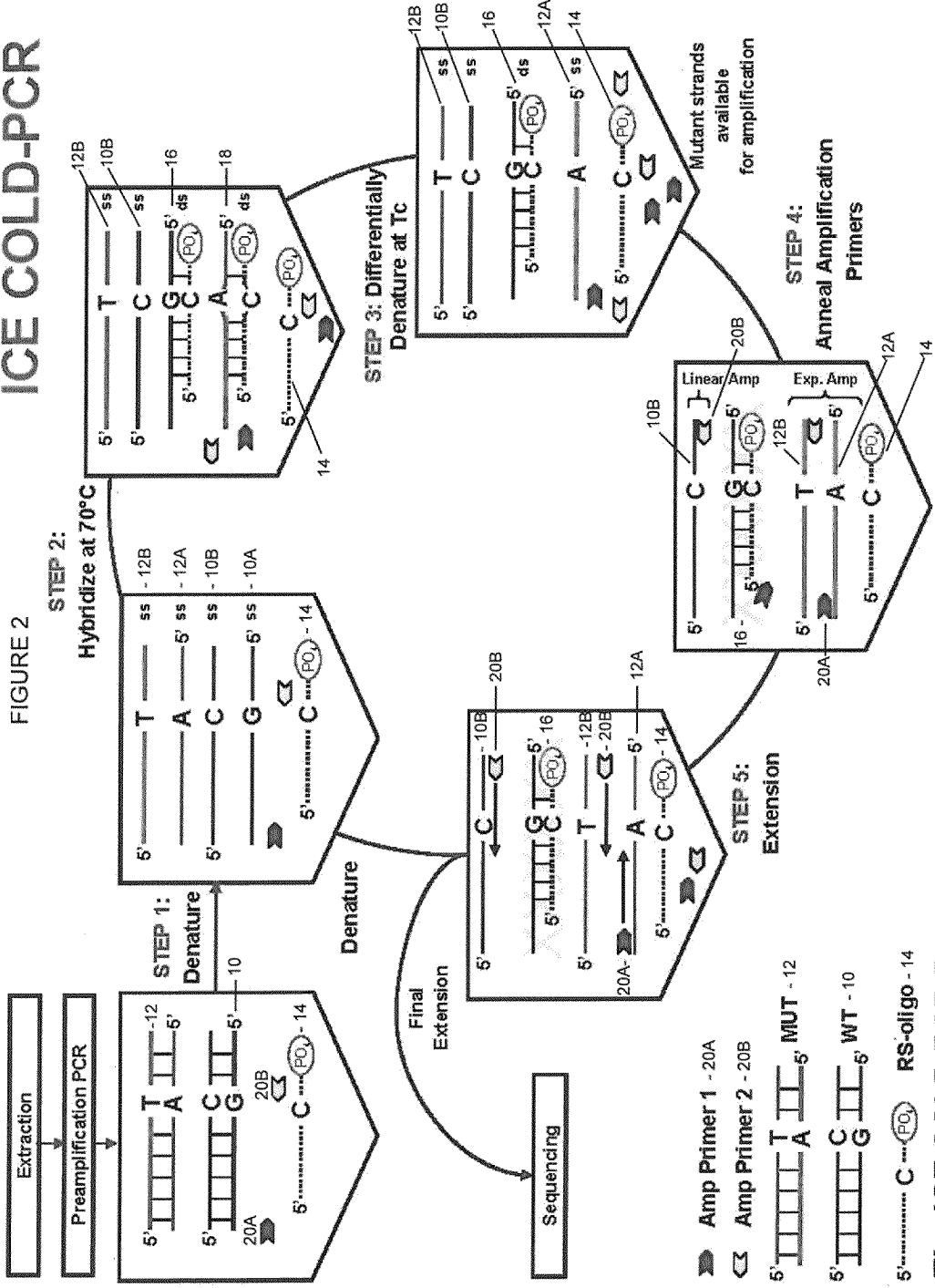

FIGURE 4

Touch-Up Fast-COLD PCR

| step | temp | time | go to |
|---|---|---|---|
| 1 | 95 °C | 4 min | 2 |
| 2 | 95 °C | 15 sec | 3 |
| 3 | 55 °C | 30 sec | 4 |
| 4 | 72 °C | 30 sec | 2, 14 times |
| 5 | 77.9 °C | 3 sec | 6 |
| 6 | 55 °C | 30 sec | 7 |
| 7 | 72 °C | 30 sec | 5, 9 times |
| 8 | 78.4 °C | 3 sec | 9 |
| 9 | 55 °C | 30 sec | 10 |
| 10 | 72 °C | 30 sec | 8, 9 times |
| 11 | 78.9 °C | 3 sec | 12 |
| 12 | 55 °C | 30 sec | 13 |
| 13 | 72 °C | 30 sec | 11, 9 times |
| 14 | 79.4 °C | 3 sec | 15 |
| 15 | 55 °C | 30 sec | 16 |
| 16 | 72 °C | 30 sec | 14, 9 times |
| 17 | 95 °C | 15 sec | 18 |
| 18 | 55 °C | 30 sec | 19 |
| 19 | 72 °C | 30 sec | 17, 4 times |
| 20 | 4 °C | 5 min | |

Fast-COLD PCR at fixed Td 78.4 °C

| step | temp | time | go to |
|---|---|---|---|
| 1 | 95 °C | 4 min | 2 |
| 2 | 95 °C | 15 sec | 3 |
| 3 | 55 °C | 30 sec | 4 |
| 4 | 72 °C | 30 sec | 2, 14 times |
| 5 | 78.4 °C | 3 sec | 6 |
| 6 | 55 °C | 30 sec | 7 |
| 7 | 72 °C | 30 sec | 5, 29 times |
| 8 | 4 °C | 5 min | |

Fast-COLD PCR at fixed Td 78.9 °C

| step | temp | time | go to |
|---|---|---|---|
| 1 | 95 °C | 4 min | 2 |
| 2 | 95 °C | 15 sec | 3 |
| 3 | 55 °C | 30 sec | 4 |
| 4 | 72 °C | 30 sec | 2, 14 times |
| 5 | 78.9 °C | 3 sec | 6 |
| 6 | 55 °C | 30 sec | 7 |
| 7 | 72 °C | 30 sec | 5, 29 times |
| 8 | 4 °C | 5 min | |

FIGURE 5

| Well | Touch Up | Fold enrichment Fast 78.4 °C | Fast 78.9 °C |
|---|---|---|---|
| A1 | 10 | No seq | No seq |
| B1 | 20 | No seq | 20 |
| C1 | 50 | No seq | 20 |
| D1 | 20 | No seq | 20 |
| E1 | 30 | No seq | 30 |
| F1 | 50 | 40 | 30 |
| G1 | 50 | 30 | 20 |
| H1 | 20 | 20 | 10 |
| A3 | 30 | No seq | |
| B3 | 30 | No seq | |
| C3 | 30 | No seq | |
| D3 | No seq | No seq | |
| E3 | 30 | No seq | |
| F3 | 30 | 20 | |
| G3 | 20 | 30 | |
| H3 | 20 | 20 | |
| A5 | 10 | No seq | No seq |
| B5 | 30 | No seq | No seq |
| C5 | 30 | No seq | No seq |
| D5 | 30 | No seq | No seq |
| E5 | 50 | No seq | 20 |
| F5 | 50 | No seq | 40 |
| G5 | 30 | 20 | 20 |
| H5 | 20 | No seq | 20 |

FIGURE 6

| Row | Calculated | | Thermocycler Mode Block | |
|---|---|---|---|---|
| | Col 7 | Col 12 | Col 7 | Col 12 |
| A | 31 | 64 | 80 | 95 |
| B | 37 | 71 | 78 | 98 |
| C | 38 | 64 | 74 | 98 |
| D | 37 | 58 | 73 | 91 |
| E | 33 | 55 | 76 | 89 |
| F | 60 | 48 | 71 | 97 |
| G | 54 | 34 | 69 | 94 |
| H | 31 | 28 | 68 | 91 |

| Step | Touch-Up Fast-COLD PCR | | |
|---|---|---|---|
| | temp | time | Go to |
| 1 | 98°C | 2 min | |
| 2 | 98°C | 15 sec | |
| 3 | 55°C | 30 sec | |
| 4 | 72°C | 30 sec | 2, 4 times |
| 5 | 80.5°C | 10 sec | |
| 6 | 55°C | 30 sec | |
| 7 | 72°C | 30 sec | 5, 4 times |
| 8 | 80.6°C | 10 sec | |
| 9 | 55°C | 30 sec | |
| 10 | 72°C | 30 sec | 8, 4 times |
| 11 | 80.7°C | 10 sec | |
| 12 | 55°C | 30 sec | |
| 13 | 72°C | 30 sec | 11, 4 times |
| 14 | 80.8°C | 10 sec | |
| 15 | 55°C | 30 sec | |
| 16 | 72°C | 30 sec | 14, 4 times |
| 17 | 80.9°C | 10 sec | |
| 18 | 55°C | 30 sec | |
| 19 | 72°C | 30 sec | 17, 9 times |
| 20 | 81.0°C | 10 sec | |
| 21 | 55°C | 30 sec | |
| 22 | 72°C | 30 sec | 20, 4 times |
| 23 | 81.1°C | 10 sec | |
| 24 | 55°C | 30 sec | |
| 25 | 72°C | 30 sec | 23, 4 times |
| 26 | 81.2°C | 10 sec | |
| 27 | 55°C | 30 sec | |
| 28 | 72°C | 30 sec | 26, 4 times |
| 29 | 81.3°C | 10 sec | |
| 30 | 55°C | 30 sec | |
| 31 | 72°C | 30 sec | 29, 4 times |
| 32 | 4°C | 5 min | |

FIGURE 7

| | | Thermocycler Column | | | | | | | |
|---|---|---|---|---|---|---|---|---|---|
| | | 48-well head | | | | | | 96-well head | | |
| | | Col 3 | Col 4 | Col 6 | | Col 7 | | | Col 12 | |
| | | TC4 | TC4 | TC4 | TC5 | Bio-Rad | TC4 | TC5 | Bio-Rad | TC4 |
| Row | | 0017hA | 0070hB | 0070hB | 0007A | | 0071A | 0007A | | 0071A |
| A | | 95 | 61 | 82 | 41 | 48 | 42 | 78 | 65 | 90 |
| B | | 86 | 38 | 82 | 56 | 35 | 28 | 89 | 61 | 83 |
| C | | 91 | 47 | 83 | 76 | 39 | 24 | 89 | 63 | 88 |
| D | | 92 | 45 | 84 | 72 | 34 | 21 | 91 | 69 | 75 |
| E | | 88 | 35 | 71 | 74 | 32 | 17 | 82 | 67 | 85 |
| F | | 88 | 28 | 57 | 68 | 33 | 20 | 62 | 68 | 90 |
| G | | 79 | 21 | 31 | 41 | 39 | 29 | 27 | 71 | 91 |
| H | | 71 | 12 | 25 | 30 | 40 | 39 | 20 | 79 | 94 |

FIGURE 8

| Row | Col 7 | | | Col 12 | | |
|---|---|---|---|---|---|---|
| | TC5 0007A | Bio-Rad | TC4 0071A | TC5 0007A | Bio-Rad | TC4 0071A |
| A | 69 | 37 | 85 | 93 | 84 | 90 |
| B | 85 | 35 | 84 | 94 | 50 | 90 |
| C | 94 | 30 | 78 | 94 | 50 | 100 |
| D | 97 | 42 | 76 | 100 | 56 | 92 |
| E | 99 | 38 | 68 | 100 | 62 | 91 |
| F | 89 | 35 | 81 | 80 | 53 | 90 |
| G | 87 | 37 | 90 | 47 | 59 | 100 |
| H | 67 | 45 | 93 | 31 | 76 | 90 |

Thermocycler Column

FIGURE 9

Touch-Up Fast-COLD PCR

| Step | Temp | Time | Go to |
|---|---|---|---|
| 1 | 98°C | 2 min | 2 |
| 2 | 98°C | 15 sec | 3 |
| 3 | 64°C | 30 sec | 4 |
| 4 | 72°C | 30 sec | 2, 4 times |
| 5 | 85.6°C | 20 sec | 6 |
| 6 | 64°C | 30 sec | 7 |
| 7 | 72°C | 30 sec | 5, 4 times |
| 8 | 85.7°C | 20 sec | 9 |
| 9 | 64°C | 30 sec | 10 |
| 10 | 72°C | 30 sec | 8, 9 times |
| 11 | 85.8°C | 20 sec | 12 |
| 12 | 64°C | 30 sec | 13 |
| 13 | 72°C | 30 sec | 11, 9 times |
| 14 | 85.9°C | 20 sec | 15 |
| 15 | 64°C | 30 sec | 16 |
| 16 | 72°C | 30 sec | 14, 9 times |
| 17 | 86.0°C | 20 sec | 18 |
| 18 | 64°C | 30 sec | 19 |
| 19 | 72°C | 30 sec | 17, 9 times |
| 20 | 86.1°C | 20 sec | 21 |
| 21 | 64°C | 30 sec | 22 |
| 22 | 72°C | 30 sec | 20, 4 times |
| 23 | 72°C | 5 min | 24 |
| 24 | 4°C | 5 min | |

Fast COLD-PCR at fixed Td 85.1 °C

| step | temp | time | go to |
|---|---|---|---|
| 1 | | 4 min | 2 |
| 2 | 95 °C | 15 sec | 3 |
| 3 | 55 °C | 30 sec | 4 |
| 4 | 72 °C | 30 sec | 2, 4 times |
| 5 | 85.1 °C | 10 sec | 6 |
| 6 | 55 °C | 30 sec | 7 |
| 7 | 72 °C | 30 sec | 5, 29 times |
| 8 | 4 °C | 5 min | |

Fast COLD-PCR at fixed Td 85.6 °C

| step | temp | time | go to |
|---|---|---|---|
| 1 | | 4 min | 2 |
| 2 | 95 °C | 15 sec | 3 |
| 3 | 55 °C | 30 sec | 4 |
| 4 | 72 °C | 30 sec | 2, 4 times |
| 5 | 85.6 °C | 10 sec | 6 |
| 6 | 55 °C | 30 sec | 7 |
| 7 | 72 °C | 30 sec | 5, 29 times |
| 8 | 4 °C | 5 min | |

FIGURE 10

| | Well | sample % mutant | Touch-Up % mutant | 85.1°C % mutant | 85.6°C % mutant |
|---|---|---|---|---|---|
| Samples without serum DNA | A7 | 100% | 100 | 100 | 100 |
| | B7 | 1% | 61 | 0 | 0 |
| | C7 | 0.50% | 43 | 0 | 0 |
| | D7 | 0.10% | 24 | 0 | 0 |
| | E7 | 0.05% | 14 | 0 | 0 |
| | F7 | 0.01% | 0 | 0 | 0 |
| | G7 | wt | 0 | 0 | 0 |
| | H7 | ntc | 0 | no seq | no seq |
| Samples with serum DNA | A8 | mut | 100 | 100 | 100 |
| | B8 | 1% | 74 | 0 | 0 |
| | C8 | 0.50% | 51 | 0 | 0 |
| | D8 | 0.10% | 18 | 0 | 0 |
| | E8 | 0.05% | 23 | no seq | 0 |
| | F8 | 0.01% | 0 | 0 | 0 |
| | G8 | wt | 0 | 0 | 0 |
| | H8 | ntc | 0 | 0 | 0 |

FIGURE 13

Touch-Up Ice-COLD-PCR

| Step | temp | time | Go to |
|---|---|---|---|
| 1 | 95°C | 2 min | 2 |
| 2 | 95°C | 15 sec | 3 |
| 3 | 57°C | 30 sec | 4 |
| 4 | 72°C | 30 sec | 2, 9 times |
| 5 | 95°C | 15 sec | 6 |
| 6 | 70°C | 2 min | 7 |
| 7 | 78.0°C | 20 sec | 8 |
| 8 | 57°C | 30 sec | 9 |
| 9 | 72°C | 30 sec | 5, 4 times |
| 10 | 95°C | 15 sec | 11 |
| 11 | 70°C | 2 min | 12 |
| 12 | 78.2°C | 20 sec | 13 |
| 13 | 57°C | 30 sec | 14 |
| 14 | 72°C | 30 sec | 11, 4 times |
| 15 | 95°C | 15 sec | 16 |
| 16 | 70°C | 2 min | 17 |
| 17 | 78.4°C | 20 sec | 18 |
| 18 | 57°C | 30 sec | 19 |
| 19 | 72°C | 30 sec | 15, 9 times |
| 20 | 95°C | 15 sec | 21 |
| 21 | 70°C | 2 min | 22 |
| 22 | 78.6°C | 20 sec | 23 |
| 23 | 57°C | 30 sec | 24 |
| 24 | 72°C | 30 sec | 20, 9 times |
| 25 | 95°C | 15 sec | 26 |
| 26 | 70°C | 2 min | 27 |
| 27 | 78.8°C | 20 sec | 28 |
| 28 | 57°C | 30 sec | 29 |
| 29 | 72°C | 20 sec | 25, 9 times |
| 30 | 95°C | 15 sec | 31 |
| 31 | 70°C | 2 min | 32 |
| 32 | 79.0°C | 20 sec | 33 |
| 33 | 57°C | 30 sec | 34 |
| 34 | 72°C | 20 sec | 30, 9 times |
| 35 | 72°C | 5 min | 36 |
| 36 | 4°C | o/n | 37 |
| 37 | 16.0°C | | |

Ice-COLD-PCR at fixed Td 78.6 °C

| Step | temp | time | Go to |
|---|---|---|---|
| 1 | 95°C | 2 min | 2 |
| 2 | 95°C | 15 sec | 3 |
| 3 | 57°C | 30 sec | 4 |
| 4 | 72°C | 30 sec | 2, 4 times |
| 5 | 95°C | 15 sec | 6 |
| 6 | 70°C | 2 min | 7 |
| 7 | 78.6°C | 10 sec | 8 |
| 8 | 57°C | 30 sec | 9 |
| 9 | 72°C | 30 sec | 5, 40 times |
| 10 | 72°C | 5 min | 11 |
| 11 | 4 °C | 5 min | |

Ice-COLD-PCR at fixed Td 79.8 °C

| Step | temp | time | Go to |
|---|---|---|---|
| 1 | 95°C | 2 min | 2 |
| 2 | 95°C | 15 sec | 3 |
| 3 | 57°C | 30 sec | 4 |
| 4 | 72°C | 30 sec | 2, 4 times |
| 5 | 95°C | 15 sec | 6 |
| 6 | 70°C | 2 min | 7 |
| 7 | 79.8°C | 10 sec | 8 |
| 8 | 57°C | 30 sec | 9 |
| 9 | 72°C | 30 sec | 5, 40 times |
| 10 | 72°C | 5 min | 11 |
| 11 | 4 °C | 5 min | |

FIGURE 14

| | Well | sample<br>% mutant | Touch-Up<br>% mutant | 78.6°C<br>% mutant | 79.8°C<br>% mutant |
|---|---|---|---|---|---|
| samples without serum DNA | A7 | wt | 0 | 0 | 0 |
| | B7 | 5% | 89 | 74 | 60 |
| | C7 | 1% | 79 | 44 | 25 |
| | D7 | 0.50% | 61 | 29 | 0 |
| | E7 | 0.10% | 50 | 0 | 0 |
| | F7 | 0.05% | 0 | 0 | 0 |
| | G7 | 0.01% | 0 | n.a. | 0 |
| | H7 | ntc | 0 | 0 | 0 |
| samples with serum DNA | A8 | wt | 0 | 0 | 0 |
| | B8 | 5% | 89 | 77 | 61 |
| | C8 | 1% | 84 | 43 | 27 |
| | D8 | 0.50% | 46 | 30 | 0 |
| | E8 | 0.10% | 0 | 19 | 0 |
| | F8 | 0.05% | 0 | 0 | 0 |
| | G8 | 0.01% | 0 | n.a. | 0 |
| | H8 | ntc | 0 | 0 | 0 |

FIGURE 15

Touch-Up Ice-COLD PCR

| Step | temp | time | Go to |
|---|---|---|---|
| 1 | 95°C | 2 min | 2 |
| 2 | 95°C | 15 sec | 3 |
| 3 | 60°C | 30 sec | 4 |
| 4 | 72°C | 30 sec | 2, 4 times |
| 5 | 95°C | 15 sec | 6 |
| 6 | 70°C | 2 min | 7 |
| 7 | 74.6°C | 20 sec | 8 |
| 8 | 60°C | 30 sec | 9 |
| 9 | 72°C | 30 sec | 5, 9 times |
| 10 | 95°C | 15 sec | 11 |
| 11 | 70°C | 2 min | 12 |
| 12 | 74.8°C | 20 sec | 13 |
| 13 | 60°C | 30 sec | 14 |
| 14 | 72°C | 30 sec | 10, 9 times |
| 15 | 95°C | 15 sec | 16 |
| 16 | 70°C | 2 min | 17 |
| 17 | 75.0°C | 20 sec | 18 |
| 18 | 60°C | 30 sec | 19 |
| 19 | 72°C | 30 sec | 15, 9 times |
| 20 | 95°C | 15 sec | 21 |
| 21 | 70°C | 2 min | 22 |
| 22 | 75.2°C | 20 sec | 23 |
| 23 | 60°C | 30 sec | 24 |
| 24 | 72°C | 30 sec | 20, 9 times |
| 25 | 95°C | 15 sec | 26 |
| 26 | 70°C | 2 min | 27 |
| 27 | 75.4°C | 20 sec | 28 |
| 28 | 60°C | 30 sec | 29 |
| 29 | 72°C | 20 sec | 25, 9 times |
| 30 | 72°C | 5 min | 31 |
| 31 | 4°C | 5 min | |

Ice-COLD PCR at fixed Td 73.8°C

| Step | temp | time | Go to |
|---|---|---|---|
| 1 | 95°C | 2 min | 2 |
| 2 | 95°C | 15 sec | 3 |
| 3 | 60°C | 30 sec | 4 |
| 4 | 72°C | 30 sec | 2, 4 times |
| 5 | 95°C | 15 sec | 6 |
| 6 | 70°C | 2 min | 7 |
| 7 | 73.8°C | 10 sec | 8 |
| 8 | 60°C | 30 sec | 9 |
| 9 | 72°C | 30 sec | 5, 40 times |
| 10 | 72°C | 5 min | 11 |
| 11 | 4°C | 5 min | |

Ice-COLD PCR at fixed Td 74.8°C

| Step | temp | time | Go to |
|---|---|---|---|
| 1 | 95°C | 2 min | 2 |
| 2 | 95°C | 15 sec | 3 |
| 3 | 60°C | 30 sec | 4 |
| 4 | 72°C | 30 sec | 2, 4 times |
| 5 | 95°C | 15 sec | 6 |
| 6 | 70°C | 2 min | 7 |
| 7 | 74.8°C | 10 sec | 8 |
| 8 | 60°C | 30 sec | 9 |
| 9 | 72°C | 30 sec | 5, 40 times |
| 10 | 72°C | 5 min | 11 |
| 11 | 4°C | 5 min | |

FIGURE 16

|  | Well | sample % mutant | Touch-Up % mutant | 73.8°C % mutant | 74.8°C % mutant |
|---|---|---|---|---|---|
| Samples without serum DNA | A7 | 0 | 0 | 0 | 0 |
|  | B7 | 5% | 100 | 63 | 37 |
|  | C7 | 1% | 100 | 79 | 84 |
|  | D7 | 0.50% | 44 | 18 | 0 |
|  | E7 | 0.10% | 0 | 0 | 0 |
|  | F7 | 0.05% | 0 | 0 | 0 |
|  | G7 | 0.01% | 0 | 0 | 0 |
|  | H7 | ntc | no seq | no seq | no seq |
| Samples with serum DNA | A8 | 0 | 0 | 0 | 0 |
|  | B8 | 5% | 100 | 59 | 33 |
|  | C8 | 1% | 100 | 80 | 80 |
|  | D8 | 0.50% | 28 | 0 | 0 |
|  | E8 | 0.10% | 0 | no seq | 0 |
|  | F8 | 0.05% | 0 | 0 | 0 |
|  | G8 | 0.01% | 0 | 0 | 0 |
|  | H8 | ntc | 0 | no seq | 0 |

SEQUENCE LISTING

```
<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
acttgtggta gttggagct                                              19

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
cctctattgt tggatcatat t                                           21

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
ctcacctcca ccgtgcaact catc                                        24

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tggctcctta tctcccctcc                                             20

<210> SEQ ID NO 5
```

-continued

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tggctcctta tctccctcc                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
gaacgtactg gtgaaaacac                                               20

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 7
gtgtcaggaa aatgctg                                                  17

<210> SEQ ID NO 8
<211> LENGTH: 49
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (30)..(31)
<223> OTHER INFORMATION: locked nucleic acid (LNA)
<220> FEATURE:
<221> NAME/KEY: misc_feature
<222> LOCATION: (33)..(34)
<223> OTHER INFORMATION: locked nucleic acid (LNA)

<400> SEQUENCE: 8
gctgtatcgt caaggcactc ttgcctacgc caccagctcc aactaccac               49

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gaaaatgctg gctgaccta                                                19

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
agttaaaatt cccgtcgcta t                                             21
```

```
<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
ttcagagcca tggaccc                                                  17
```

STEP-UP METHOD FOR COLD-PCR ENRICHMENT

CROSS-REFERENCE TO RELATED APPLICATIONS

This patent application claims the benefit of priority of U.S. Provisional Patent Application No. 61/647,970, filed May 16, 2012, which is incorporated herein by reference in its entirety.

REFERENCE TO SEQUENCE LISTING SUBMITTED VIA EFS-WEB

This application includes an electronically submitted Sequence Listing in .txt format. The .txt file contains a sequence listing entitled "2013-05-05 5472-00040_ST25.txt" created on May 5, 2013 and is 2,550 bytes in size. The Sequence Listing contained in this .txt file is part of the specification and is hereby incorporated by reference herein in its entirety.

FIELD OF THE INVENTION

The invention pertains to improvements to the amplification and enrichment of low prevalence target sequences, e.g. mutations, in nucleic acid samples. In particular, the invention pertains to robust step-up methods for implementing full (with or without a reference blocking sequence) or fast COLD-PCR (CO-amplification at Lower Denaturation temperature).

BACKGROUND OF THE INVENTION

A commonly encountered situation in genetic analysis entails the need to identify a low percent of variant DNA sequences ("target sequences") in the presence of a large excess of non-variant sequences ("reference sequences"). Examples for such situations include: (a) identification and sequencing of a few mutated alleles in the presence of a large excess of normal alleles; (b) identification of a few methylated alleles in the presence of a large excess of unmethylated alleles (or vice versa) in epigenetic analysis; (c) detection of low levels of heteroplasmy in mitochondrial DNA; (d) detection of drug-resistant quasi-species in viral, bacterial or parasitic infections and (e) identification of tumor-circulating DNA in blood of cancer patients (where people are suspected of having cancer, to track the success of cancer treatment or to detect relapse) in the presence of a large excess of wild-type alleles.

COLD-PCR methods for enriching the concentration of low abundance alleles in a sample PCR reaction mixture were initially described in a published patent PCT application entitled "Enrichment of a Target Sequence", International Application No. PCT/US2008/009248, now U.S. Ser. No. 12/671,295, by Gerassimos Makrigiorgos which is incorporated herein by reference. The described COLD-PCR enrichment methods are based on a modified nucleic acid amplification protocol which incubates the reaction mixture at a critical denaturing temperature "$T_c$". The prior patent application discloses two formats of COLD-PCR, namely full COLD-PCR and fast COLD-PCR.

In full COLD-PCR, the reaction mixture is subjected to a first denaturation temperature (e.g., 94° C.) which is chosen to be well above the melting temperature for the reference (e.g., wild-type) and target (e.g., mutant) sequences similar to conventional PCR. Then, the mixture is cooled (e.g., to 70° C.) to facilitate the formation of reference-target heteroduplexes by hybridization. In the basic full COLD-PCR method, lowering of the temperature from the first denaturing temperature (e.g., 94° C.) to the hybridization temperature (e.g., 70° C.) over a relatively long time period (e.g., 8 minutes) or retaining the reaction mixture at the hybridization temperature for a relatively long time period (e.g., 70° C. for 8 min) is required to assure proper hybridization. Once cooled, the reaction mixture contains not only reference-target heteroduplexes but also reference-reference homoduplexes (and to a lesser extent target-target homoduplexes). When the target sequence and reference sequence cross hybridize, minor sequence differences of one or more single nucleotide mismatches or insertions or deletions anywhere along a short (e.g., <200 bp) double stranded DNA sequence will generate a small but predictable change in the melting temperature ($T_m$) for that sequence (Lipsky, R. H., et al. (2001) Clin Chem, 47, 635-644; Liew, M., et al. (2004) Clin Chem, 50, 1156-1164). Depending on the exact sequence context and position of the mismatch, melting temperature changes of 0.1-20° C., are contemplated. Full COLD-PCR, as described in the above referred patent application, is premised on the difference in melting temperature between the double stranded reference sequence and the hybridized reference-target heteroduplexes. After cooling down to form reference-target heteroduplexes, the reaction mixture is incubated at a critical denaturing temperature ($T_c$), which is chosen to be less than the melting temperature for the double stranded reference sequence and higher than the lower melting temperature of the reference-target heteroduplexes, thereby preferentially denaturing the cross hybridized target-reference heteroduplexes over the reference-reference homoduplexes.

The critical denaturing temperature ($T_c$) is a temperature below which PCR efficiency drops abruptly for the reference nucleic acid sequence (yet is sufficient to facilitate denaturation of the reference-target heteroduplexes). For example, a 167 bp p53 sequence amplifies well if the PCR denaturing temperature is set at 87° C., amplifies modestly at 86.5° C. and yields no detectable product if PCR denaturation is set at 86° C. or less. Therefore, in this example the selected $T_c$ should be ~86.5° C. or less. After intermediate incubation at the critical denaturing temperature ($T_c$), the primers are then annealed to the denatured target and reference strands from the denatured heteroduplexes (e.g., 55° C.) and extended by a polymerase (e.g., 70° C.), thus enriching the concentration of the target sequence relative to the reference sequence. One of the advantages of full COLD-PCR is that the same primer pair is used for both target and reference sequences.

The above described full COLD-PCR method requires significant cycle times to ensure suitable cross-hybridization of reference-target heteroduplexes and has also otherwise proven to be somewhat inefficient. To address these issues, Makrigiorgos has described the use of reference blocking sequences to improve the efficiency and reduce cycle time of full COLD-PCR, see Full COLD-PCR Enrichment with Reference Blocking Sequence, International Application No. PCT/US2011/027473, published as Publication No. WO2011/112534, filed on Mar. 8, 2011, which is also incorporated herein by reference. This modified, full COLD-PCR method using reference blocking sequences is referred to as "RBS full COLD-PCR" for purposes herein. In the RBS full COLD-PCR method, reference blocking sequence is added at an excess concentration level to the amplification reaction mixture. The reference blocking sequence is a nucleic acid sequence complementary with at least a portion of one of the strands of the reference sequence between its primer binding sites, or partly overlapping the primer binding sites. The reference blocking sequence added to the reaction mixture is desirably single stranded (but can also be double stranded inasmuch as the initial denaturing step will result in denatured, single stranded reference blocking sequences). The reaction mixture is subjected to a first denaturing temperature, e.g. 95° C., which is above the melting temperature ($T_m$) of the reference sequence and also the target sequence, and results in denatured strands of the reference sequence and the target sequence. The reaction mixture is cooled to promote hybridization, for example to about 70° C. Since the cooling down occurs in the presence of an excess amount of reference blocking sequences, the reference blocking sequences preferentially hybridize with the complementary strand of the reference sequence, and also the complementary strand of the target sequence. For example, assuming that single stranded reference blocking sequence is added in excess at the beginning of the process, the reaction mixture at this point in the process will contain heteroduplexes of the reference blocking sequences and the complementary reference (e.g., wild-type) strand and heteroduplexes of the reference blocking sequences and the target (e.g. mutant) strands. The reaction mixture at this point also contains the denatured negative strands for the reference and target sequences. The formed heteroduplexes present in the RBS full COLD-PCR cycle are fundamentally different from the reference-target heteroduplexes formed in the unmodified full COLD-PCR protocol. Supplying an excess amount of reference blocking sequence promotes faster hybridization (e.g., about 30 seconds) than in the unmodified full COLD-PCR protocol (e.g., about 8 minutes); and the cool down hybridization step in the RBS full COLD-PCR protocol is less than one minute in duration.

In the RBS full COLD-PCR method, the reaction mixture is then subjected to a critical temperature (e.g., $T_c$=84.5° C.) which is sufficient to permit preferential denaturation of the target strands from the reference blocking sequence. The melting temperature for the duplex of the reference blocking sequence and the target strands will always be less than the melting temperature of the duplex of the reference blocking sequence and the complementary reference strand because the former contains a mismatch whereas the latter does not. The critical temperature ($T_c$) is selected so that duplexes of the reference blocking strands and the complementary reference strands remain substantially undenatured when the reaction mixture is incubated at $T_c$ yet duplexes of the reference blocking strands and the target strands substantially denature. The term "substantially" means at least 60%, and preferably at least 90% or more preferably at least 98% in a given denatured or undenatured form.

After preferential denaturation, the temperature of the reaction mixture is reduced (e.g. 55° C.) so as to permit the primer pairs to anneal to the free target and reference strands in the reaction mixture. Again, assuming that single stranded reference blocking oligonucleotides are added in excess at the beginning of the process, at this point in the cycle there are, theoretically, two free strands of the target sequence compared to the initial denaturation step and only one free reference strand. The other reference strand is hybridized with the reference blocking sequence, and is therefore unavailable for amplification. The annealed primers are then extended (e.g., 70° C.), thus resulting in exponential amplification of the target sequence, while the reference strand is only amplified linearly. Accordingly, the target sequence is gradually enriched relative to the reference sequence in the sample during the full COLD-PCR cycles. The above steps are likely repeated ten to thirty cycles or more.

The reference blocking sequence is desirably at least several bases smaller than the target and reference sequences, on each side of the sequence so that the primers do not bind appreciably to the reference sequence and so that the reference blocking sequence is not extended by the primers that amplify the target sequence. To this end, optionally the 3' OH end of the reference blocking sequence can be blocked to DNA-polymerase extension. Also, optionally, the 5'-end of the reference blocking sequence may be designed such that the nucleotide sequence partially overlaps the primer binding sites such that 5' to 3' exonucleolysis by Taq DNA polymerases (i.e. degradation of the hybridized reference blocking sequence) may be prevented.

Fast COLD-PCR, as described in the above incorporated patent application, International Application No. PCT/US2008/009248, now U.S. Ser. No. 12/671,295, by Gerassimos Makrigiorgos, is premised on there being a difference in melting temperature between the double stranded reference sequence (e.g., wild-type sequence) and the double stranded target sequence (e.g., mutant sequence). In particular, the melting temperature of the target sequence must be lower than the reference sequence. The critical denaturing temperature ($T_c$) in fast COLD-PCR is a temperature at or below which PCR efficiency drops abruptly for the double stranded reference nucleic acid sequence, yet is still sufficient to facilitate denaturation of the double stranded target sequence. During the fast COLD-PCR enrichment cycle, the reaction mixture is not subjected to denaturation at a temperature (e.g., 94° C.) above the melting temperature of the reference sequence as in the first step of the full COLD-PCR cycle. Rather, the reaction mixture is incubated at a critical denaturing temperature (e.g., $T_c$=83.5° C.), which is chosen either (a) to be less than the melting temperature for the double stranded reference sequence and higher than the lower melting temperature of the double stranded target sequence, or; (b) to be lower than the $T_m$ of both reference and target sequences, whilst still creating a differential between the degree of denaturation of reference and target sequences. After incubation at the critical denaturing temperature ($T_c$), the primers are annealed to the denatured target strands and extended by a polymerase, thus enriching the concentration of the target sequence relative to the reference sequence. Again, the same primer pair is used for both target and reference sequences.

The use of fast COLD-PCR is limited to applications in which the melting temperature of the double stranded target sequence is suitably less than the melting temperature for the double stranded reference sequence. For example, mutations will not be detectable in sequencing data for a sample with a low abundance of mutant sequences that has been subjected to fast COLD-PCR if the melting temperature of the mutant sequence is the same or higher than the melting temperature of the wild-type sequence.

SUMMARY OF THE INVENTION

The PCR methods summarized above require very precise temperature control during the PCR amplification cycles to ensure that well-to-well variation is minimized. Provided herein are methods of minimizing well-to-well variation in methods of enriching the amplification of target sequences in the background of related reference sequences. In particular, these methods allow the use of PCR machines with block-based temperature control to be used with PCR enrichment methods. The methods are also useful to limit the differences in temperature between PCR machines or the effects of these temperatures when different reagents, amplification mixture amounts or plasticware, such as PCR tubes are used to in PCR enrichment procedures such as those described herein. The methods provided herein compensate of well-to-well, PCR run-to-run and lab-to-lab variations in the PCR reactions and make the PCR enrichment assays more robust and amenable to widespread use in a variety of laboratory environments.

Methods for enriching a target sequence in an amplification reaction mixture are provided herein. The methods are referred to herein as step-up or touch-up PCR methods interchangeably. In one embodiment, the methods include preparing an amplification reaction mixture with at least the following constituents: a primer pair capable of amplifying a reference sequence and a nucleic acid sample having the reference sequence and also suspected of having one or more target sequences that are at least 50% homologous to said reference sequence and are also amplifiable by the same primer pair as said reference sequence and with the target sequence being less prevalent than the reference sequence. A critical temperature ($T_c$) is selected such that it is sufficient to permit preferential denaturation of heteroduplexes of a strand of the reference sequence and a strand of the target sequence yet insufficient to denature homoduplexes of the reference sequence. Second denaturing temperatures ($T_{d2}$) for multiple sets of amplification cycles are selected such that the second denaturing temperature ($T_{d2}$) for a first set of amplification cycles is less than the selected critical temperature ($T_c$) and the second denaturing temperature ($T_{d2}$) for subsequent sets of amplification cycles are progressively higher than the previous set of amplification cycles. Then for each set of amplification cycles, the following steps are cycled through to enrich the target sequence in the amplification reaction mixture. First, the amplification reaction mixture is subjected to a first denaturing temperature ($T_{d1}$) that is above the melting temperature ($T_m$) of the reference sequence and the target sequence to form reference strands and target strands. Then the temperature of the amplification reaction mixture is reduced to permit formation of heteroduplexes of the reference strands and the target strands. The temperature of the amplification reaction mixture is then increased to the selected second denaturing temperature ($T_{d2}$). The temperature of the amplification reaction mixture is reduced again to permit said primer pair to anneal to target strands and reference strands in the amplification reaction mixture and the primer pair is extended to enrich said target sequence relative to said reference sequence. The amplification cycle is then repeated a set number of times using said selected second denaturing temperatures ($T_{d2}$) for the respective set of amplification cycles.

In another embodiment, the methods include preparing an amplification reaction mixture with at least the following constituents: a primer pair capable of amplifying a reference sequence and a nucleic acid sample having the reference sequence and also suspected of having one or more target sequences that are at least 50% homologous to said reference sequence and are also amplifiable by the same primer pair as said reference sequence and a molar excess of a reference blocking sequence relative to the amount of reference sequence, the reference blocking sequence is fully complementary with at least a portion of the sequence of one of the strands of the reference sequence between or overlapping its primer binding sites, and the target sequence is less prevalent than the reference sequence. A critical temperature ($T_c$) is selected such that it is sufficient to permit preferential denaturation of heteroduplexes of the reference blocking sequence and target strands yet insufficient to denature duplexes of the reference blocking sequence and complementary strands of the reference sequence. Second denaturing temperatures ($T_{d2}$) for multiple sets of amplification cycles are selected such that the second denaturing temperature ($T_{d2}$) for a first set of amplification cycles is less than the selected critical temperature ($T_c$) and the second denaturing temperature ($T_{d2}$) for subsequent sets of amplification cycles are progressively higher than the previous set of amplification cycles. Then for each set of amplification cycles, the following steps are cycled through to enrich the target sequence in the amplification reaction mixture. First, the amplification reaction mixture is subjected to a first denaturing temperature ($T_{d1}$) that is above the melting temperature ($T_m$) of the reference sequence and the target sequence to form reference strands and target strands. Then the temperature of the amplification reaction mixture is reduced to permit formation of heteroduplexes of the reference blocking sequence and the complementary reference strands and heteroduplexes of the reference blocking sequence and the target strands. The temperature of the amplification reaction mixture is then increased to the selected second denaturing temperature ($T_{d2}$). The temperature of the amplification reaction mixture is reduced again to permit said primer pair to anneal to target strands and reference strands in the amplification reaction mixture and the primer pair is extended to enrich said target sequence relative to said reference sequence. The amplification cycle is then repeated a set number of times using said selected second denaturing temperatures ($T_{d2}$) for the respective set of amplification cycles.

In another embodiment, the methods include preparing an amplification reaction mixture with at least the following constituents: a primer pair capable of amplifying a reference sequence and a nucleic acid sample having the reference sequence and also suspected of having one or more target sequences that are at least 50% homologous to said reference sequence and the target sequence having a melting temperature below the melting temperature of said reference sequence and also amplifiable by the same primer pair as said reference sequence. A critical temperature ($T_c$) is selected such that it is sufficient to permit preferential denaturation of the target sequence yet insufficient to substantially denature the reference sequence. Second denaturing temperatures ($T_{d2}$) for multiple sets of amplification cycles are selected such that the second denaturing temperature ($T_{d2}$) for a first set of amplification cycles is less than the selected critical temperature ($T_c$) and the second denaturing temperature ($T_{d2}$) for subsequent sets of amplification cycles are progressively higher than the previous set of amplification cycles. Then for each set of amplification cycles, the following steps are cycled through to enrich the target sequence in the amplification reaction mixture. First, the temperature of the amplification reaction mixture is increased to the selected second denaturing temperature ($T_{d2}$). Then the temperature of the amplification reaction mixture is reduced to permit said primer pair to anneal to target strands in the amplification reaction mixture and the primer pair is extended to enrich said target sequence relative to said reference sequence. The amplification cycle is then repeated a set number of times using said selected second denaturing temperatures ($T_{d2}$) for the respective set of amplification cycles.

Other embodiments and advantages of the invention may be apparent to those skilled in the art upon reviewing the drawings and the following detailed description.

BRIEF DESCRIPTION OF THE DRAWINGS

FIG. 1 illustrates a prior art embodiment of full COLD-PCR for selectively enriching a target sequence as described in the prior patent application entitled "Enrichment of a Target Sequence", International Application No. PCT/US2008/009248, now U.S. Ser. No. 12/671,295, and incorporated herein by reference.

FIG. 2 illustrates a second prior art embodiment of ICE COLD PCR or Full COLD PCR in the presence of a reference blocking sequence which improves full COLD PCR via the presence of an excess amount of a reference blocking sequence in the amplification reaction mixture. See Full COLD PCR Enrichment with Reference Blocking Sequence, International Application No. PCT/US2011/027473, published as Publication No. WO2011/112534, filed on Mar. 8, 2011.

FIG. 4 is a set of tables showing a comparison of standard and step-up FAST COLD PCR protocols for detection of KRAS Exon 2 G12S.

FIG. 5 is a table showing improved enrichment of a FAST COLD PCR by using the step-up method described in FIG. 4.

FIG. 6 is a set of Tables. The left table shows the step-up FAST COLD PCR protocol used for enrichment of the target sequence and the right panel shows the fold enrichment of the target sequence in the calculated vs. the block mode of the thermocycler.

FIG. 7 is a table showing the fold enrichment achieved using the step-up PCR protocol for FAST COLD PCR in 8 well strips.

FIG. 8 is a table showing the fold enrichment achieved using the step-up PCR protocol for FAST COLD PCR in 96 well plates.

FIG. 9 is a set of tables showing a comparison of standard and step-up FAST COLD PCR protocols for selection of EGFR Exon 20 T790M.

FIG. 10 is a table showing a summary of the results of the protocols described in FIG. 9 using various DNA inputs and target sequence amounts.

FIG. 13 is a set of tables showing a comparison of standard and step-up ICE COLD PCR protocols for detection of EGFR Exon 21 L858R.

FIG. 14 is a table showing a summary of the results of the protocols described in FIG. 13 using various DNA samples and target sequence amounts.

FIG. 15 is a set of tables showing a comparison of standard and step-up ICE COLD PCR protocols for EGFR Exon 19 ΔE746.

FIG. 16 is a table showing a summary of the results of the protocols described in FIG. 15 using various DNA samples and target sequence amounts.

DETAILED DESCRIPTION

Definitions

Figure 3:
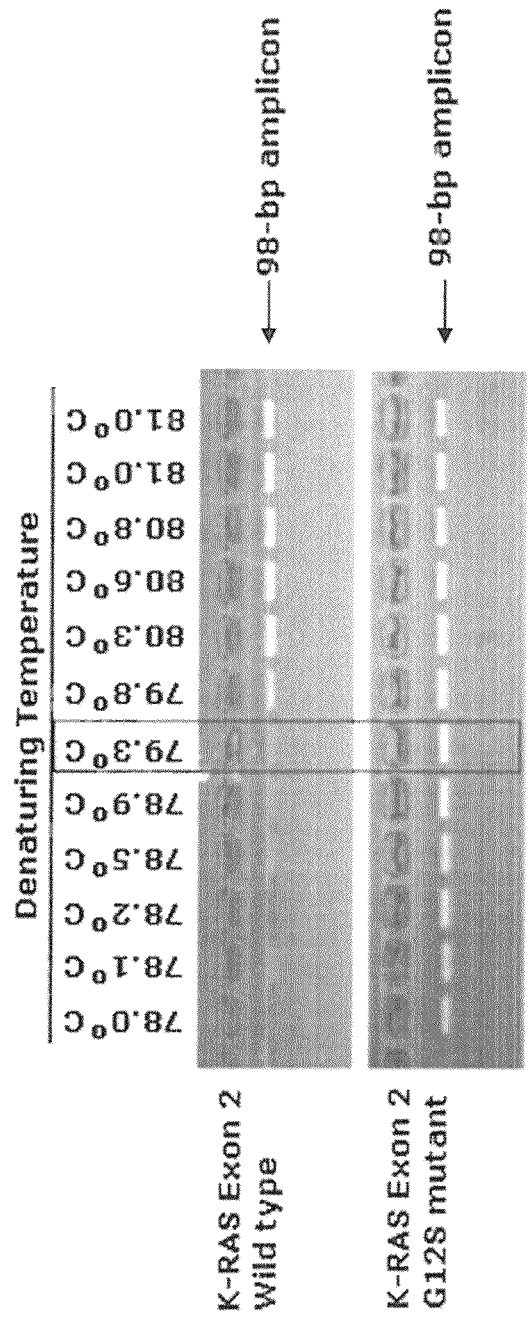
FIG. 3 is a photograph of a gel after a PCR reaction to determine the Tc for a FAST COLD PCR reaction for detection of KRAS Exon 2 G12S.

As used herein, the term "enriching a target sequence" refers to increasing the amount of a target sequence and increasing the ratio of target sequence relative to the corresponding reference sequence in a sample. For example, where the ratio of target sequence to reference sequence is initially 5% to 95% in a sample, the target sequence may be preferentially amplified in an amplification reaction so as to produce a ratio of 70% target sequence to 30% reference sequence. Thus, in this Example there is a 14 fold enrichment of the target sequence relative to the reference sequence.

As used herein the term "target sequence" refers to a nucleic acid that is less prevalent in a nucleic acid sample than a corresponding reference sequence. The target sequence makes-up less than 50% of the total amount of reference sequence+target sequence in a sample. The target sequence may be a mutant allele. For example, a sample (e.g., blood sample) may contain numerous normal cells and few cancerous cells. The normal cells contain non-mutant or wild-type alleles, while the small number of cancerous cells contains somatic mutations. In this case the mutant is the target sequence while the wild-type sequence is the reference sequence. As used herein, a "target strand" refers to a single nucleic acid strand of a double-stranded target sequence.

The target sequence must be at least 50% homologous to the corresponding reference sequence, but must differ by at least one nucleotide from the reference sequence. Target sequences are amplifiable via PCR with the same pair of primers as those used for the reference sequence.

As used herein, the term "reference sequence" refers to a nucleic acid that is more prevalent in a nucleic acid sample than a corresponding target sequence. The reference sequence makes-up over 50% of the total reference sequence+target sequence in a sample. Preferably the reference sequence is expressed at the RNA and/or DNA level 10×, 15×, 20×, 25×, 30×, 35×, 40×, 45×, 50×, 60×, 70×, 80×, 90× 100×, 150×, 200× or more than the target sequence. As used herein, a "reference strand" refers to a single nucleic acid strand of a double-stranded reference sequence.

As used herein, the term "wild-type" refers to the most common polynucleotide sequence or allele for a certain gene in a population. Generally, the wild-type allele will be obtained from normal cells. The wild-type is generally the reference sequence.

As used herein, the term "mutant" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The invention is broadly concerned with somatic mutations and polymorphisms. The methods of the invention are especially useful in selectively enriching a mutant allele which contains between about 1 and 10 nucleotide sequence changes, although it is useful even with a higher number of sequence changes. A mutant allele will typically be obtained from diseased tissues or cells and is associated with a disease state.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words the $T_m$ is defined as the temperature at which 50% of the nucleotides of two complementary sequences are annealed (double strands) and 50% of the nucleotides are denatured (single strands). $T_m$, therefore defines a midpoint in the transition from double-stranded to single-stranded nucleic acid molecules (or, conversely, in the transition from single-stranded to double-stranded nucleic acid molecules).

The $T_m$ can be estimated by a number of methods, for example by a nearest-neighbor calculation as per Wetmur 1991 (Wetmur, J. G. 1991. DNA probes: applications of the principles of nucleic acid hybridization. Crit Rev Biochem Mol Biol 26: 227-259,) and by commercial programs including Oligo™ Primer Design and programs available on the internet. Alternatively, the $T_m$ can be determined though actual experimentation. For example, double-stranded DNA binding or intercalating dyes, such as Ethidium bromide or SYBR-green (Molecular Probes) can be used in a melting curve assay to determine the actual $T_m$ of the nucleic acid. Additional methods for determining the $T_m$ of a nucleic acid are well known in the art. Some of these methods are listed in the inventor's prior patent application entitled "Enrichment of a Target Sequence", International Application No. PCT/US2008/009248, now U.S. Ser. No. 12/671,295, incorporated by reference herein.

As used herein, "reference blocking sequence" is an engineered single stranded or double stranded nucleic acid sequence, such as an oligonucleotide and preferably has a length smaller than the amplified section of the target sequence. In a preferred embodiment, the reference blocking sequence is several bases smaller than the amplified section of the reference sequence, on each side of the sequence so that the primers do not bind appreciably to the reference sequence. In another embodiment, the reference blocking sequence may overlap with a primer binding site. Optionally, the 3' OH end of the reference blocking sequence is blocked to DNA-polymerase extension. Optionally, the 5'-end is modified to prevent 5' to 3' exonucleolysis by Taq DNA polymerases. The reference blocking sequence can also take other forms which remain annealed to the reference sequence when the reaction mixture is subject to the critical temperature "$T_c$", such as a chimera between single stranded DNA, RNA, peptide nucleic acid (PNA) or locked nucleic acid (LNA), or another modified nucleotide. In one embodiment, a PNA or LNA is used in the reference blocking sequence at a position at which the nucleotide in the reference sequence differs from that in the target sequence. Such a construction will increase the difference in the melting temperature of the reference blocking sequence-reference sequence and the reference blocking sequence-target sequence heteroduplexes to further favor denaturation of reference blocking sequence-target sequence heteroduplexes at the $T_c$ and enrichment of the target sequence.

As used in connection with the present invention, the term "critical temperature" or "$T_c$" refers to a temperature selected to preferentially denature duplexes of target strands and the reference blocking sequence as compared to the reference blocking sequence-reference strand duplexes. The critical temperature ($T_c$) is selected so that duplexes consisting of the reference blocking strands and complementary reference strands remain substantially undenatured when the reaction mixture is incubated at $T_c$ yet duplexes consisting of the reference blocking strands and the target strands substantially denature. The term "substantially" means at least 60%, and preferably at least 90% or more preferably at least 98% in a given denatured or undenatured form. In the examples provided below, the selected critical temperature "$T_c$" for the intermediate incubation step is 84.5° C., whereas the first denaturing temperature is 95° C.

As used herein, "primer pair" refers to two primers that anneal to opposite strands of a target and reference sequence so as to form an amplification product during a PCR reaction. The target and the reference sequence should be at least 25 bases in order to facilitate primer attachment. The primer pair is designed so as to have a $T_m$ lower than the $T_c$ of the reaction.

As used herein, "homology" refers to the subunit sequence similarity between two polymeric molecules, e.g., two polynucleotides or two polypeptides. An example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215: 403-410 (1990), respectively.

Software for performing BLAST analyses is publicly available through the National Center for Biotechnology Information.

Nucleic Acid Amplification Generally

In one embodiment, a nucleic acid sample utilized in the method of the invention comprises genomic DNA having a reference sequence and either known to have or suspected of having a target sequence. In another embodiment, the nucleic acid sample of the method of the invention comprises target and reference sequences that were previously amplified in a nucleic acid amplification reaction. The skilled artisan will appreciate that there are many methods available to amplify a nucleic acid. Perhaps the most popular method is the polymerase chain reaction (PCR; for example, see, U.S. Pat. Nos. 4,683,195 and 4,683,202, as well as Saiki et al., Science 230:1350-1354 (1985) and Gyllensten et al., PNAS (USA) 85:7652-7656 (1985)). A preferred variation of the PCR method is asymmetrical PCR (for example, see Mao et al., Biotechniques 27(4):674-678 (1999); Lehbein et al., Electrophoresis 19(8-9):1381-1384 (1998); Lazaro et al., Molec. Cell. Probes 6(5):357-359 (1992); and U.S. Pat. No. 6,197, 499). Other amplification methods include, but are not limited to, strand displacement amplification (SDA) (see, Walker et al., Nuc. Acids Res. 20(7):1691-1696 (1992), as well as U.S. Pat. Nos. 5,744,311, 5,648,211 and 5,631,147), rolling circle amplification (RCA) (see PCT publication WO 97/19193), nucleic acid sequence-based amplification (NASBA) (see Compton, Nature 350:91-92 (1991); as well as U.S. Pat. Nos. 5,409,818 and 5,554,527), transcript mediated amplification (TMA) (see Kwoh et al., PNAS (USA) 86:1173-1177 (1989), as well as U.S. Pat. No. 5,399,491), self sustained sequence replication (3SR) (see Guatelli et al., PNAS (USA) 87:1874-1879 (1990) and ligase chain reaction (LCA) (see U.S. Pat. Nos. 5,427,930 and 5,792,607).

In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of at least 10$^9$ relative to other sequences in genomic DNA. The PCR method is also described in Saiki et al., 1985, *Science* 230:1350.

PCR is performed using template DNA (target and reference sequences) (at least 1 fg; more usefully, 1-1000 ng) and generally 25 pmol of oligonucleotide primers. A typical reaction mixture includes: 2 μl of DNA, 25 pmol of oligonucleotide primers, 2.5 μl of a suitable buffer, 0.4 μl of 1.25 μM dNTPs, 2.5 units of Taq DNA polymerase (Stratagene) and deionized water to a total volume of 25 μl. PCR is generally performed using a programmable thermal cycler. Those of skill in the art appreciate that PCR reactions can be larger or smaller, contain additional components such as dimethyl sulfoxide (DMSO) or bovine serum albumin (BSA) to improve amplification or specificity of the reaction and be performed using various methodologies.

The length and temperature of each step of a PCR cycle, as well as the number of cycles, are adjusted according to the stringency requirements in effect for a particular reaction. Annealing temperature and timing are determined both by the efficiency with which a primer is expected to anneal to a template and the degree of mismatch that is to be tolerated. The ability to optimize the stringency of primer annealing conditions is well within the knowledge of one of ordinary skill in the art. An annealing temperature of between 30° C. and 72° C. is generally used. Initial denaturation of the template molecules normally occurs at between 92° C. and 99° C. for 1-5 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

PCR utilizes a nucleic acid polymerase, or enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase. In the methods described herein, generally RNA would be reverse transcribed to DNA prior to use in the methods.

The enrichment procedures of the present invention are performed in a PCR device such as a thermocycler, or under real-time reaction conditions in a real-time PCR device. Real-time or quantitative reaction conditions further utilize a nucleic acid detection agent (e.g., dye or probe) in order to measure/detect the PCR product as it is produced.

Samples

As used herein, "sample" refers to any substance containing or presumed to contain a nucleic acid of interest (target and reference sequences) or which is itself a nucleic acid containing or presumed to contain a target nucleic acid of interest. The term "sample" thus includes a sample of nucleic acid (genomic DNA, cDNA, RNA, mRNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

Nucleic acid sequences of the invention can be amplified from genomic DNA. Genomic DNA can be isolated from tissues or cells according to the following method or an alternative method. Such methods are well known in the art. Alternatively nucleic acids sequences of the invention can be isolated from blood or another fluid by methods well known in the art.

To facilitate detection of a variant form of a gene from a particular tissue, the tissue is isolated or harvested. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used according to the invention.

The target DNA may also be extracted from whole blood. For example, blood may be drawn by standard methods into a collection tube, preferably comprising siliconized glass, either without anticoagulant for preparation of serum, or with EDTA, sodium citrate, heparin, or similar anticoagulants, most preferably EDTA, for preparation of plasma. The preferred method, although not absolutely required, is that plasma or serum be fractionated from whole blood. Plasma or serum may be fractionated from whole blood by centrifugation, preferably gentle centrifugation at 300 to 800×g for 5-10 minutes, or fractionated by other standard methods. Since heparin may interfere with PCR, use of heparinized blood may require pretreatment with heparinase. Thus, EDTA is the preferred anticoagulant for blood specimens. Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use. The DNA may then be extracted by methods well known in the art.

The methods may also be used with an RNA or mRNA sample. Methods for isolating RNA or mRNA are well known in the art. One such method is the RNAzol B method (Tel-Test, Friendswood, Tex.). The RNA may be converted into DNA using a reverse transcriptase. The DNA may then be used in the PCR reactions.

The method of the present invention can be used to detect whether methylation has occurred or is absent in a target sequence. The methylation detection method comprises a chemical or enzymatic approach for methylation-sensitive treatment of DNA. Chemical treatments include the incubation of DNA with sodium bisulfite, which selectively converts non-methylated cytosines to uracils. The DNA is first heat-denatured and then treated with 5M bisulfite, pH 5-7. Pretreatment of genomic DNA to remove pre-existing uracils is used prior to bisulfite treatment. This pretreatment consists of uracil glycosylase treatment in the presence of 5 mM hydroxylamine, pH 7.

Because the methylated cytosines of the treated target or reference sequence are converted to uracils, they will now form mismatches when duplexed with the unmethylated target or reference sequences or with the reference blocking sequence in the hybridization cool down step of full COLD-PCR (or in the presence of reference blocking sequence).

Full COLD-PCR in the Absence of Reference Blocking Sequence (Prior Art)

FIG. 1 illustrates the prior art procedure known as full COLD-PCR for enriching a target sequence in a nucleic acid sample containing a target and reference sequence, which is disclosed in the above incorporated U.S. application Ser. No. 12/671,295, entitled "Enrichment of a Target Sequence". FIG. 1 is a reproduction of FIG. 1 in the above incorporated patent application.

The target and reference sequences can be obtained from a variety of sources including, but not limited to, genomic DNA, cDNA, viral DNA or RNA, mammalian DNA, fetal DNA, mitochondrial DNA or bacterial DNA. While the reference sequence is generally the wild-type allele and the target sequence is the mutant allele, the reverse may also be true. The mutant allele may include one or more nucleotide deletions, insertions or alterations. In some embodiments, the mutant allele is a somatic mutation. In other embodiments, the target sequence is methylated DNA while the reference sequence is un-methylated DNA or vice versa.

The method includes subjecting the amplification reaction mixture to a first denaturing temperature (FIG. 1A, Step 1) that is above the melting temperature "$T_m$" of a reference sequence. The $T_m$ of a nucleic acid can be determined through experimentation or estimated by calculation. The skilled artisan is well aware of numerous well known methods for determining the $T_m$ of a nucleic acid some of which are described herein. The first denaturing temperature is generally selected as one would generally select the denaturing temperature of a PCR reaction and should be sufficiently high so as to allow the full denaturing of the target and reference sequences (e.g., 94° C.). In one embodiment, the first denaturing temperature is about 1° C. to 30° C. above the $T_m$ of the reference sequence, more preferably the $T_m$ of the reference sequence is about 5° C. to 20° C. above the $T_m$ of the reference sequence.

Next, the temperature of the amplification reaction mixture is decreased allowing the target sequences and reference sequences to hybridize (FIG. 1A, Step 2). This annealing step results in the formation of duplexes of target-target, reference-reference and target-reference sequences, but should be optimized to form target-reference duplexes. The PCR primers used in the method are designed to have a melting temperature that prevents them from binding to the target and reference sequences at this intermediate temperature. Suitably, either the amount of time to transition from the denaturation temperature to the temperature to allow cross-hybridization or the amount of time the sample is kept at the hybridization temperature is generally greater that one minute, suitably more than 4 minutes, suitably more than 6, 8 or even 10 minutes. As mentioned above, the requirement of target-reference hybridization and the relatively large amount of time needed for cool down (FIG. 1A, Step 2) has been found to limit the effectiveness of full COLD-PCR in at least some applications.

The target-reference hybridization duplexes are then preferentially denatured by increasing the temperature of the reaction mixture to the $T_c$ (FIG. 1A, Step 3). The $T_c$ or critical temperature in FIG. 1 is selected to be below the $T_m$ of the reference sequence yet near, at, or above the $T_m$ of the target-reference duplex. As mentioned previously, when the target sequence and reference sequence cross hybridize, minor sequence differences of one or more single nucleotide mismatch anywhere along a double stranded DNA sequence will generate a small but predictable change in the melting temperature ($T_m$) for that sequence (Lipsky, R. H., et al. (2001) *Clin Chem*, 47, 635-644; Liew, M., et al. (2004) *Clin Chem*, 50, 1156-1164). Depending on the exact sequence context and position of the mismatch, melting temperature changes in the range of 0.1-20° C. are possible. The $T_c$ is generally applied (FIG. 1A, Step 3) from about 1 second to 5 minutes, more preferably 5 seconds to 30 seconds. It is possible to oscillate between steps 3 and 2 for multiple cycles if desired.

After the preferential denaturing of the target-reference hybridization duplexes, the temperature of the reaction mixture is reduced so as to allow one or more primers to anneal to the target sequence (FIG. 1A, Step 4). The annealed primers are then extended by a nucleic acid polymerase (FIG. 1A, Step 5), thus enriching the target sequence in the population of nucleic acids contained in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, i.e. a thermal cycler, more preferably under real-time reaction conditions in a real-time detection PCR device, such as the SMARTCY-CLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a labeled probe i.e., an oligonucleotide operatively coupled to a fluorescent dye) for quantifying and/or monitoring the amplification products of the reaction. Once the enrichment of the target sequence is complete the sample may be further processed, e.g., subjected to a sequencing reaction. The enriched alleles may be further processed by a variety of procedures including: MALDI-TOF, HR-Melting, Di-deoxy-sequencing, Single-molecule sequencing, second generation high throughput sequencing, pyrosequencing, RFLP, digital PCR and quantitative-PCR (See FIG. 1B). A more detail description of these processing technologies as well as diagnostic assays is included in the above mentioned U.S. application Ser. No. 12/671,295, entitled "Enrichment of a target Sequence", and incorporated herein by reference.

Full COLD-PCR with Excess Reference Blocking Sequence in Reaction Mixture

FIG. 2 illustrates the prior art procedure known as full cold PCR with reference blocking sequences to enrich a target sequence in a nucleic acid sample in accordance with the method described in International Publication No. WO2011/112534 as described above and incorporated herein by reference in its entirety. To begin (FIG. 2, step 1), the nucleic acid sample contains a double-stranded reference sequence 10 (e.g., a wild-type sequence) and contains a double-stranded target sequence 12 (e.g., a mutant sequence). The amplification reaction mixture contains the sample, other PCR ingredients, and in accordance with the invention a reference blocking sequence 14 at an excess concentration level. The reference blocking sequence is suitably added to the reaction mixture such that there is a molar excess of the reference blocking sequence as compared to the reference sequence and the target sequence. In some embodiments, the reference blocking sequence is present in the reaction mixture at a concentration of at least 10 nM, 20 nM, 25 nM, 30 nM, 40 nM, 50 nM, 75 nM, or even 100 nM. Suitably the reference blocking sequence is present in molar excess to the reference sequence and the target sequence. In FIG. 2, the depicted reference blocking sequence 14 is a single-stranded nucleic acid sequence complementary with one of the strands 10A of the reference sequence 10 between its primer binding sites or overlapping a primer binding site.

The reaction mixture in step 1 of FIG. 2 is subjected to a first denaturing temperature, e.g. 95° C. for 30 seconds, which results in denatured strands of the reference sequence 10A, 10B and the target sequence 12A, 12B. The reaction mixture is then cooled to promote hybridization, e.g., 70° C. for 30 seconds, which is a dramatic reduction from the normal 8 minute cool down used in full cold PCR. Since the cool down occurs in the presence of an excess amount of reference blocking sequences 14, the reference blocking sequences 14 preferentially hybridize with the complementary strand 10A of the reference sequence and also the complementary strand 12A of the target sequence. Step 2 in FIG. 2 illustrates the state of the reaction mixture after the hybridization cool down to 70° C. In addition to heteroduplexes 16 of the reference blocking sequence 14 and the complementary reference strand 10A and heteroduplexes 18 of the reference blocking sequence 14 and the complementary target strand 12A, the reaction mixture also contains the denatured negative strands 10B and 12B of the reference and target sequences, respectively.

In step 3 of FIG. 2, the reaction mixture is then subjected to the critical temperature "$T_c$", e.g., 84.5° C., which is chosen to permit preferential denaturation of the heteroduplexes 18 of the target strand 12A and reference blocking sequence 14. The critical temperature ($T_c$) is selected so that duplexes 16 of the reference blocking strands 14 and the complementary reference strands 10A remain substantially undenatured when the reaction mixture is incubated at "$T_c$". The melting temperature for the duplex 18 of the reference blocking sequence 14 and the target strand 10B will always be less than the melting temperature of the duplex 16 of the reference blocking sequence 14 and the complementary reference strand 10A because the reference blocking sequence 14 is fully complementary with at least a portion of the reference strand 10A, and there will be at least one mismatch with the target strand 12A.

Referring to step 4 of FIG. 2, after preferential denaturation, the temperature of the reaction mixture is reduced, e.g., 60° C., to permit the primer pair 20A, 20B to anneal to the free target strands 12A, 12B and the free reference strand 10B in the reaction mixture. Reference number 20A refers to the forward primer and reference number 20B refers to the reverse primer. As described previously, the target sequence 12 is amplifiable via the same pair of primers 20A, 20B as those used for the reference sequence 10. Step 5 of FIG. 2 illustrates two free strands 12A, 12B of the target sequence compared to the initial denaturation step and only one free reference strand 10B. The other reference strand 10A is hybridized with the reference blocking sequence 14, and is therefore unavailable for amplification. The temperature of the reaction mixture is then raised, e.g. 72° C., to extend the annealed primers 20A, 20B, thus enriching the concentration of the target sequence 12 in the reaction mixture relative to the reference sequence 10. The method is likely repeated five to thirty cycles, suitably 10-40 cycles.

The method illustrated in FIG. 2 can and should be optimized for individual protocols. Such protocols can be embodied in software, if desired, for operating various PCR and real-time PCR equipment.

Design Considerations for the Preferred Reference Blocking Sequence

As mentioned, the reference blocking sequence can take many forms, yet the preferred form is single stranded, non-extensible DNA. More specifically, the preferred reference blocking sequence has the following characteristics:

(a) comprises single-stranded DNA of up to 200 bp in length;
(b) has a length that is several bases smaller than the target sequence (e.g. 8-12 bases on each side of the sequence) so that the primers do not bind appreciably to the reference sequence when annealed to the reference blocking sequence; and also do not bind appreciably to the reference blocking sequence itself; and
(c) contains a 3'-end that is blocked to DNA-polymerase extension.

Such a reference blocking sequence can be synthesized in one of several methods. First, the reference blocking sequence can be made by direct synthesis using standard oligonucleotide synthesis methods that allow modification of the 3'-end of the sequence. The 3'-end may contain a phosphate group, an amino-group, a di-deoxy-nucleotide or any other moiety that blocks 5' to 3' polymerase extension. Alternatively, the reference blocking sequence can be made by polymerase synthesis during a PCR reaction that generates single stranded DNA as the end product. In this case, the generated single stranded DNA corresponds to the exact sequence necessary for the reference blocking sequence. Methods to synthesize single stranded DNA via polymerase synthesis are several and well known to those skilled in the art. For example, asymmetric PCR or LATE PCR would be suitable. Alternatively, a single stranded DNA reference blocking sequence can be synthesized by binding double stranded PCR product on solid support. This is accomplished by performing a standard PCR reaction, using a primer pair one of which is biotinylated. Following PCR, the PCR product is incubated with a streptavidin-coated solid support (e.g. magnetic beads) and allowed to bind to the beads. Subsequently, the temperature is raised to 95° C. for 2-3 minutes to denature DNA and release to the solution the non-biotinylated DNA strand from the immobilized PCR product. The magnetic beads with the complementary DNA strand are then removed and the single stranded product remaining in the solution serves as the reference blocking sequence.

Before the single stranded reference blocking sequence is used, the 3'-end is preferably blocked to polymerase extension. This can be accomplished in several ways well known to those skilled in the art. For example, a reaction with Terminal Deoxynucleotide Transferase (TdT) can be employed, in the presence of di-deoxy-nucleotides (ddNTP) in the solution, to add a single ddNTP to the end of the single stranded reference blocking sequence. ddNTPs serve to block polymerase extension. Alternatively, an oligonucleotide template complementary to the 3'-end of the reference blocking sequence can be used to provide a transient double stranded structure. Then, polymerase can be used to insert a single ddNTP at the 3'-end of the reference blocking sequence opposite the hybridized oligonucleotide.

In another method to synthesize the reference blocking sequence in a double stranded form, a conventional PCR is carried out to amplify a wild type version of the sequence of interest, using primers that contain rare enzymatic restriction sites. Following PCR amplification, restriction enzymes are applied to digest both ends of the PCR product and create overhangs. These overhangs are then subjected to polymerase extension in the presence of di-deoxy-nucleotides, thereby blocking the 3'-end on both sides from further extension. The double-stranded, 3'-end blocked PCR product can then serve as a double stranded reference blocking sequence.

The reference blocking sequence may include a cap or other modified nucleotide on the 5' end that is capable of blocking or preventing 5' to 3' exonucleolysis by a DNA polymerase, such as Taq. Those skilled in the art are aware of modifications that will render the 5' end resistant to exonucleolysis. Examples of modifications that will render the reference blocking sequence resistant to exonucleolysis are as follows: the 5' end of the reference blocking sequence may comprise a 2'-O-methyl nucleotide or a 5' cap (i.e. addition of a 7'-methylguanylate to the 5' end).

The reference blocking sequence may be single-stranded or double-stranded DNA or RNA, and may contain modified nucleic acids such as peptide nucleic acids (PNA), or locked nucleic acids (LNA) or a chimera of any of the above. If a double-stranded reference blocking sequence is used, it will be denatured to form single-stranded reference blocking sequences in the initial denaturing step of the PCR methods described herein. If a modified nucleotide, LNA or PNA is present in the reference blocking sequence, the position of the modified nucleotide, LNA or PNA may be selected to match at least one position where a mutation (i.e. a difference in sequence between the target and reference sequences) is suspected to be present. By selecting this position for incorporation of the modified nucleotide in the reference blocking sequence, the difference between the temperature needed to denature duplexes of the reference blocking sequence and the complementary reference strand and that required to denature heteroduplexes of the reference blocking sequence and the partially complementary target sequence is maximized.

The reference blocking sequence may be fully complementary with one strand of the reference sequence between it primer binding sites or partially overlapping the primer binding sites. Suitably, the reference blocking sequence may be fully complementary with a portion of the reference sequence. Suitably, the reference blocking sequence is shorter than the reference sequence and comprises less than 300 bases, 250 bases, 200 bases, 150 bases, 125 bases, 100 bases, 90 bases, 80 bases, 70 bases, 60 bases, 50 bases, 40 bases, 30 bases. Suitably the reference blocking sequence is longer than 20 bases, 30 bases, 40 bases, 50 bases, 60 bases, 70 bases, 80 bases, 90 bases, 100 bases, 125 bases, 150 bases, 175 bases or 200 bases.

FAST COLD PCR Method

Fast COLD-PCR, as described in the above incorporated patent application, International Application No. PCT/US2008/009248, now U.S. Ser. No. 12/671,295, by Gerassimos Makrigiorgos, is premised on there being a difference in melting temperature between the double stranded reference sequence (e.g., wild-type sequence) and the double stranded target sequence (e.g., mutant sequence). In particular, the melting temperature of the target sequence must be lower than the reference sequence. The critical denaturing temperature ($T_c$) in fast COLD-PCR is a temperature below which PCR efficiency drops abruptly for the double stranded reference sequence, yet is still sufficient to facilitate denaturation of the double stranded target sequence. During the fast COLD-PCR enrichment cycle, the reaction mixture is not subjected to denaturation at a temperature (e.g., 94° C.) above the melting temperature of the reference sequence as in the first step of the full COLD-PCR cycle. Rather, the reaction mixture is incubated at a critical denaturing temperature (e.g., $T_c$=83.5° C.), which is chosen either (a) to be less than the melting temperature for the double stranded reference sequence and higher than the lower melting temperature of the double stranded target sequence, or; (b) to be lower than the $T_m$ of both reference and target sequences, whilst still creating a differential between the degree of denaturation of reference and target sequences. The Tc or critical temperature can be determined by the methods described herein. In one embodiment, the Tc is about 0.3° C.-5° C. below the $T_m$ of the reference sequence and more preferably about 0.5° C. to 1.5° C. below the $T_m$ of the reference sequence. Generally, the Tc will be about 70-90° C. The Tc is generally applied from about 1 second to 5 minutes, more preferably 2 seconds to 1 minute and most preferably 5 seconds to 30 seconds. At the Tc, the target sequence duplexes are substantially denatured, whereas the reference sequence duplexes are substantially undenatured. "Substantially" means at least 40%, preferably at least 50%, preferably at least 60%, preferably at least 70%, more preferably at least 80%, even more preferably at least 90% and most preferably at least 98% in a given denatured or undenatured form.

After incubation at the critical denaturing temperature ($T_c$), the primers are annealed to the denatured target strands and extended by a polymerase, thus enriching the concentration of the target sequence relative to the reference sequence. Again, the same primer pair is used for both target and reference sequences. The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art.

The use of fast COLD-PCR is limited to applications in which the melting temperature of the double stranded target sequence is suitably less than the melting temperature for the double stranded reference sequence. For example, mutations will not be detectable in sequencing data for a sample with a low abundance of mutant sequences that has been subjected to fast COLD-PCR if the melting temperature of the mutant sequence is the same or higher than the melting temperature of the wild-type sequences.

Step-Up Methods of Full or Fast COLD PCR

In Full and Fast COLD PCR, incubation of the target and reference sequences (in Fast COLD PCR) or alternatively of the formed heteroduplexes (in Full COLD PCR) is carried out at a single critical temperature for all reaction mixtures in the assay and for each round of amplification. The appropriate $T_c$ to allow the best enrichment of the target sequences by each of these methods may represent a very narrow range of temperatures in some cases. Variations between thermal cyclers or between wells of a single thermal cycler may lead to insufficient or inconsistent enrichment of amplification of target sequences as compared to reference sequences or may limit the detection of small amounts of the target sequence in a background of large amounts of the reference sequence. The methods described herein may be implemented in multiple PCR reaction tubes placed in a thermal cycler being operated in block mode. The methods allow for enrichment of the target sequence even if there is well-to-well variation in the precise temperatures during the reactions. The multiple PCR tubes may be part of an integral plate or strip.

The methods provided herein address these issues by using sets of amplification cycles with different denaturation temperatures used in place of the $T_c$. These denaturation temperatures are referred to as second denaturing temperatures ($T_{d2}$). The $T_{d2}$ used in the first set of amplification cycles is less than the $T_c$. The $T_{d2}$ used in subsequent sets of amplification cycles is chosen to be progressively higher than the previous $T_{d2}$. Suitably, the final $T_{d2}$ used in a set of amplification reactions in the methods described herein is at least equal to or greater than the $T_c$. The $T_{d2}$ may be adjusted in equal temperature increments between each set of amplification cycles. Alternatively, the $T_{d2}$ may be adjusted in non-equal increments.

The step-up methods described herein include more than one set of amplification cycles. A set of amplification cycles may include 2 or more amplification cycles, 3 or more amplification cycles, suitably 5 or more amplification cycles, suitably 7 or more amplification cycles, suitably 10 or more amplification cycles. A set of amplification cycles may include 2-30 cycles, 4-25 cycles, 5-20 cycles, or 7-15 cycles. The step-up methods include at least two sets of amplification cycles. Suitably, the methods include at least 3, 4, 5, 6, 7, 8, 9 or even 10 sets of amplification cycles.

The second denaturing temperature ($T_{d2}$) used in sets of amplification cycles may be defined by the following equation: $T_{d2}=T_{d2i}+k\Delta$, where $T_{d2i}$ is the second denaturing temperature selected for the initial set of amplification cycles; $\Delta$ is a fixed temperature increment between sets of amplification cycles; k is an index indicating the respective cycle set (k=1, 2, 3 . . . K), and K represents the total number of cycle sets. The $T_{d2}$ selected for the initial set of amplification cycles may be substantially equal to the selected $T_c$ or it may be at least 0.1° C., 0.2° C., 0.3° C., 0.4° C., 0.5° C., 0.7° C., 0.8° C., 1° C., 2° C. or even more less than the $T_c$. The temperature increment between sets of amplification cycles may be at least 0.1° C., 0.2° C., 0.4, 0.5° C., 0.7° C., 0.8° C., 1.0° C., 1.2° C., 1.5° C., 1.7° C., or 2.0° C.

In the step-up methods described herein, the target and reference sequences in the nucleic acid sample may be amplified by an amplification method such as PCR prior to inclusion in the methods. The PCR may be completed by using the first denaturing temperature that is higher than the melting temperature of the reference sequence such that both the reference sequence and the target sequence are amplified. PCR may also be used after the step-up methods described herein to further amplify the nucleic acids in the sample after the enrichment procedure. The methods described herein may also be followed by analysis of the amplification reaction mixture using a mutation detection method. Those skilled in the art will appreciate that many methods may be used to analyze a sample for a particular (i.e. target) nucleic acid. Such methods include, but are not limited to, MALDI-TOF, HR-Melting, Di-deoxy-sequencing, Single-molecule sequencing, pyrosequencing, Second generation high-throughput sequencing, SSCP, RFLP, dHPLC, CCM, digital PCR and quantitative-PCR. These methods may be useful for detecting target sequences that represent a mutant allele of the reference sequence comprising a deletion, insertion or alteration of one or more nucleotides.

The methods described herein may be performed in a quantitative or real-time PCR device. The reaction mixture may contain a nucleic acid detection agent, such as a nucleic acid detection dye (e.g., SYBR Green) or a labeled probe (e.g., a TaqMan probe or other oligonucleotide labeled with a fluorescent marker). The methods described herein may also be used to enrich two or more different target sequences and the target sequences may be amplifiable with the same primer pair or with different primer pairs. Such a reaction may include more than one nucleic acid detection agent.

In the Full COLD methods described herein the $T_c$ may be above, equal to, or below the $T_m$ of the reference sequence. In the Fast-cold PCR methods described herein the $T_c$ must be below the $T_m$ of the reference sequence, but may be above, equal to or below the $T_m$ of the target sequence. Suitably, the $T_c$ is between 0.3° C. and 5° C. below the $T_m$ of the reference sequence. Suitably, the primer pair has a melting temperature that is below the $T_c$ and suitably below the $T_{d2}$. Optionally, the annealing temperature of the primers is at least 5° C. below the $T_c$. The steps of the step-up PCR methods may be carried out for various periods of time between 1 second and 15 minutes for each step of the method. The length of time for which the $T_{d2}$ is applied is generally between 1 second and 5 minutes. Suitably the length of time for this step is 10 seconds, 20 seconds, 30 seconds, 40 seconds, 50 seconds, 1 minute or more. Suitably, the length of time for this step is 5 minutes, 4 minutes, 3 minutes, 2 minutes, 1 minute or less.

Full COLD Step-Up Method

A step-up method of Full COLD PCR for enriching a target sequence in an amplification reaction mixture is provided herein. In the Full COLD methods described herein, the melting temperature of the double-stranded target sequence may be less than, greater than or equal to the melting temperature of the double-stranded reference sequence. The method includes preparing an amplification reaction mixture including at least a primer pair capable of amplifying a reference sequence and the target sequence and a nucleic acid sample having the reference sequence and suspected of having one or more target sequences that are at least 50% homologous to the reference sequence. A critical temperature ($T_c$) sufficient to permit preferential denaturation of heteroduplexes of a strand of the reference sequence and a strand of the target sequence yet insufficient to denature homoduplexes of the reference sequence must be selected or experimentally determined. Based on the $T_c$, second denaturing temperatures ($T_{d2}$) for multiple sets of amplification cycles must then be selected. The second denaturing temperature ($T_{d2}$) for the first set of amplification cycles is suitably less than the selected critical temperature ($T_c$) and the second denaturing temperature ($T_{d2}$) for subsequent sets of amplification cycles should be progressively higher than that used in the previous set of amplification cycles. Each set of amplification cycles is carried out as described below and the method includes at least two sets of amplification cycles carried out using at least two distinct second denaturing temperatures.

For each set of amplification cycles, the following steps are cycled through in order to enrich the target sequence in the amplification reaction mixture. First, the amplification reaction mixture is subjected to a first denaturing temperature ($T_{d1}$) that is above the melting temperature ($T_m$) of the reference sequence and the target sequence to form reference strands and target strands. Then, the temperature of the amplification reaction mixture is reduced to permit formation of heteroduplexes of the reference strands and the target strands. The temperature of the amplification reaction mixture is then increased to the selected second denaturing temperature ($T_{d2}$) for a set of amplification cycles. The temperature of the amplification reaction mixture is then reduced to permit the primer pair to anneal to any free target strands and reference strands in the amplification reaction mixture. The temperature of the amplification reaction mixture is then selected to allow extension of the primer pair to enrich said target sequence relative to said reference sequence.

Each of the steps of the method can be held for various amounts of time. In the Full-cold PCR method, the step of allowing the denatured reference strands and target strands to form heteroduplexes of reference strands and target strands may be allowed a long period of time to allow for effective heteroduplex formation. Suitably this step is greater than one minute, optionally between 1 minute and 15 minutes, suitably greater than 2 minutes, greater than 3 minutes, greater than 4 minutes, greater than 5 minutes, greater than 6 minutes, greater than 7 minutes, greater than 8 minutes or even greater than 10 minutes. In the Full COLD methods, the steps of reducing the temperature of the reaction mixture to form heteroduplexes of the reference strands and target strands and then increasing the temperature of the reaction mixture to the second denaturing temperature to preferentially denature the target strand-reference strand heteroduplexes as compared to reference strand homoduplexes may be repeated more than one time prior to proceeding to the step of primer annealing and extension.

Full COLD Step-Up Method with Reference Blocking Sequence

A step-up method of Full COLD PCR with a reference blocking sequence for enriching a target sequence in an amplification reaction mixture is provided herein. In the methods described herein, the melting temperature of the double-stranded target sequence may be less than, greater than or equal to the melting temperature of the double-stranded reference sequence. The methods include preparing an amplification reaction mixture including at least a primer pair capable of amplifying a reference sequence and the target sequence and a nucleic acid sample having the reference sequence and suspected of having one or more target sequences that are at least 50% homologous to the reference sequence. The amplification mixture also includes a molar excess amount of a reference blocking sequence relative to the amount of reference sequence. The characteristics of the reference blocking sequences for use in the methods are described above. A critical temperature ($T_c$) sufficient to permit preferential denaturation of heteroduplexes of the reference blocking sequence and a strand of the target sequence yet insufficient to substantially denature duplexes of the reference blocking sequence and the complementary strand of the reference sequence must be selected or experimentally determined. Based on the $T_c$, second denaturing temperatures ($T_{d2}$) for multiple sets of amplification cycles must then be selected. The second denaturing temperature ($T_{d2}$) for the first set of amplification cycles is suitably less than the selected critical temperature ($T_c$) and the second denaturing temperature ($T_{d2}$) for subsequent sets of amplification cycles should be progressively higher than that used in the previous set of amplification cycles. Each set of amplification cycles is carried out as described below and the method includes at least two sets of amplification cycles carried out using at least two distinct second denaturing temperatures.

For each set of amplification cycles, the following steps are cycled through in order to enrich the target sequence in the amplification reaction mixture. First, the amplification reaction mixture is subjected to a first denaturing temperature ($T_{d1}$) that is above the melting temperature ($T_m$) of the reference sequence and the target sequence to form reference strands and target strands. Then, the temperature of the amplification reaction mixture is reduced to permit formation of heteroduplexes of the reference blocking sequence and reference strands and of the reference blocking sequence and target strands. The temperature of the amplification reaction mixture is then increased to the selected second denaturing temperature ($T_{d2}$) for a set of amplification cycles. The temperature of the amplification reaction mixture is then reduced to permit the primer pair to anneal to any free target strands and reference strands in the amplification reaction mixture. The amplification reaction mixture temperature is then increased to allow extension of the primer pair to enrich said target sequence relative to said reference sequence.

Each of the steps of the method can be held for various amounts of time. In the Full-cold PCR method including a reference blocking sequence, the step of allowing the denatured reference strands and target strands to form heteroduplexes with the reference blocking sequence may be carried out for a relatively short period of time to allow for effective heteroduplex formation. Suitably, this step is held for less than one minute, optionally this step is held for more than 1 second. Suitably, the step is held for 10 seconds, 20 seconds, 30 seconds, 40 seconds or more. Suitably this step is held for 4 minutes, 3 minutes, 2 minutes, 1 minute, 45 seconds, 30 seconds or less. In these methods, the steps of reducing the temperature of the reaction mixture to form heteroduplexes of the reference blocking sequence with the reference strands and target strands and then increasing the temperature of the reaction mixture to the second denaturing temperature to preferentially denature the target strand-reference blocking sequence heteroduplexes as compared to reference strand—reference blocking sequence duplexes may be repeated more than one time prior to proceeding to the step of primer annealing and extension.

FAST COLD PCR Step-Up Method

A step-up method of Fast COLD PCR for enriching a target sequence in an amplification reaction mixture is provided herein. In the Fast COLD methods described herein, the melting temperature of the double-stranded target sequence must be less than the melting temperature of the double-stranded reference sequence. The method includes preparing an amplification reaction mixture including at least a primer pair capable of amplifying a reference sequence and the target sequence and a nucleic acid sample having the reference sequence and suspected of having one or more target sequences that are at least 50% homologous to the reference sequence. A critical temperature ($T_c$) sufficient to permit preferential denaturation of the target sequence as compared to the reference sequence must be selected or experimentally determined. Based on the $T_c$, second denaturing temperatures ($T_{d2}$) for multiple sets of amplification cycles must then be selected. The second denaturing temperature ($T_{d2}$) for the first set of amplification cycles is suitably less than the selected critical temperature ($T_c$) and the second denaturing temperature ($T_{d2}$) for subsequent sets of amplification cycles should be progressively higher than that used in the previous set of amplification cycles. Each set of amplification cycles is carried out as described below and the method includes at least two sets of amplification cycles carried out using at least two distinct second denaturing temperatures.

For each set of amplification cycles, the following steps are cycled through in order to enrich the target sequence in the amplification reaction mixture. First, the temperature of the amplification reaction mixture is increased to the selected second denaturing temperature ($T_{d2}$) for a set of amplification cycles. The temperature of the amplification reaction mixture is then reduced to permit the primer pair to anneal to any free target strands and reference strands in the amplification reaction mixture. The temperature of the amplification reaction mixture is then selected to allow extension of the primer pair to enrich said target sequence relative to said reference sequence. After completion of one set of amplification cycles at the selected $T_{d2}$, further cets of amplification cycles at progressively higher $T_{d2}$ temperatures are completed.

Also provided are computer readable media with program instructions for performing the methods described herein. The computer readable media may include methods of calculating the $T_c$, the $T_{d2}$ and/or the $T_m$ of the target, reference and reference blocking sequences. The media may also include instructions capable of directing a PCR machine or thermal cycler, including a real-time PCR machine to carry out the steps of the method.

The following examples are meant only to be illustrative and are not meant as limitations on the scope of the invention or of the appended claims. All references cited herein are hereby incorporated by reference in their entireties.

EXAMPLES

Example 1

FAST COLD PCR for Determination of Presence of KRAS Exon 2 G12S Mutation

The first step was to determine the Critical Temperature ($T_c$) needed to enrich a KRAS Exon 2 G12S 98-bp amplicon.

The results of this empirical determination of the $T_c$ are shown in FIG. 3. The PCR was carried out with Taq DNA polymerase, Forward primer 5'ACTTGTGGTAGTTG-GAGCT3' (SEQ ID NO: 1) and reverse primer 5'CCTCTAT-TGTTGGATCATATT3' (SEQ ID NO: 2). PCR amplification was carried out in an MJ Gradient thermocycler and consisted of an initial denaturation at 95° C. for 2 minutes, followed by 15 cycles of standard amplification at 95° C. for 15 seconds, 55° C. for 30 seconds and 72° C. for 30 seconds. The initial PCR was followed by 30 cycles of COLD PCR amplification with denaturation at temperatures between 78.0° C. and 81.0° C. as shown in FIG. 3 for 10 seconds, annealing at 55° C. for 30 seconds and extension at 72° C. for 30 seconds. The empirical $T_c$ is shown in a rectangle as 79.3° C. in FIG. 3.

FAST COLD PCR was then carried out using the traditional FAST COLD method at two different $T_c$s ($T_d$) or using the step-up methods described herein as shown in the Table in FIG. 4. In each case, the PCR was carried out on a thermal cycler using the calculated mode rather than the block mode. FIG. 5 shows the fold enrichment of the target sequence as compared to the reference sequence when the starting DNA population contained 10% target sequence.

Example 2

FAST COLD PCR for Determination of Presence of KRAS Exon 2 G12D Mutation

Similar experiments using the primers described in Example 1 were performed to enrich a KRAS Exon 2 G12D amplicon in different thermal cyclers using either 8-tube strips or 96 well plates for the amplification reaction mixtures. As shown in FIG. 6, 1% KRAS Exon 2 mutant G12D was enriched in 8-tube strips in an MJ Research PTC-200 thermal cycler. The left panel of FIG. 6 shows the Step-up Fast COLD PCR protocol used for mutant enrichment and the right panel shows the fold-enrichment of the mutant molecules in the Calculated versus Block Mode in two different columns of the thermal cycler. The use of the block mode in combination with the step-up process allows for greater enrichment of the target sequence.

FIG. 7 shows the fold enrichment achieved by Step-up Fast COLD PCR of 1% KRAS Exon 2 mutant G12D in 8-tubes strips. MJ Research PTC-200 thermal cyclers (TC4 and TC5 in the table) with 48-well heads (0017hA or 0070hB, and 0007A and 0071A) and a BioRad S-1000 thermal cycler were used to enrich a 1% G12D KRAS Exon 2 mutant in a wild-type background in 8-tube strips using the Step-up Fast COLD PCR protocol shown in FIG. 6.

FIG. 8 shows the fold enrichment achieved by Step-up Fast COLD-PCR of 1% K-RAS Exon 2 mutant G12D in 96-well plates. MJ Research PTC-200 thermocyclers (TC4 and TC5 in the table) with 96-well heads (0007A or 0071A) and a BioRad S-1000 thermal cycler with a 96-well head were used to enrich a 1% G12D KRAS Exon 2 mutant in a wild-type background in 96-well plates using the Step-up Fast COLD PCR protocol described in FIG. 6.

Example 3

FAST COLD PCR for Determination of Presence of EGFR Exon 20 T790M Mutation

A FAST COLD PCR method for the EGFR Exon 20 T790M mutation was previously developed. The primers for use in the reaction are as follows: Forward Primer: 5'-CT-CACCTCCACCGTGCAACTCATC-3' (SEQ ID NO: 3); Reverse Primer: 5'-TGGCTCCTTATCTCCCCTCC-3' (SEQ ID NO: 4). In FIG. 9, Fast COLD PCR protocols at a fixed denaturation temperature ($T_d$) are shown on the left and a Step-up Fast COLD PCR protocol is on the right. Fixed temperature protocols were carried out in the thermocycler Calculated Mode, while the Step-up Fast COLD PCR protocol was carried out in the Block Mode. The $T_c$ for EGFR Exon 20 under the experimental conditions used was 85.6° C.

Figure 11:
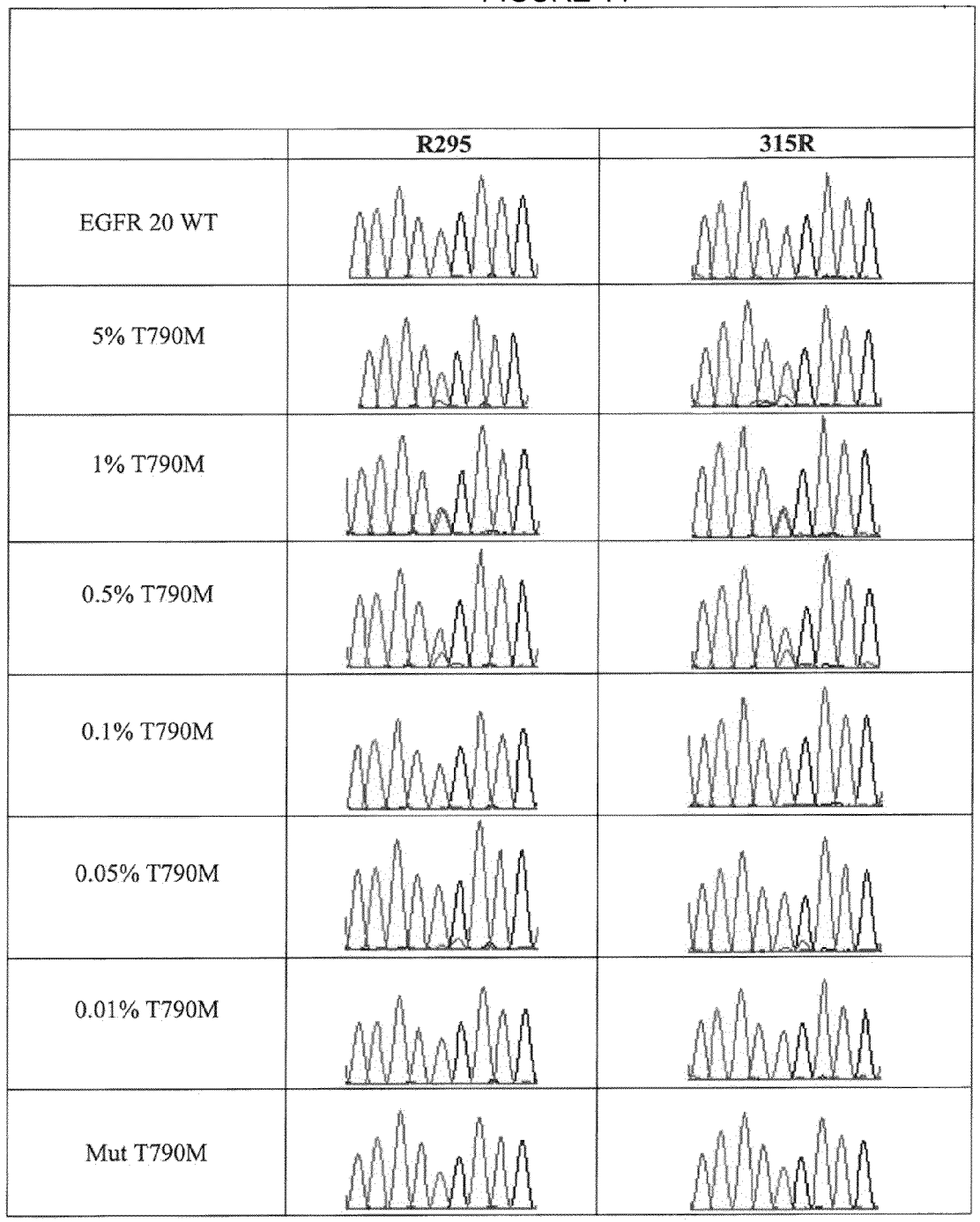
FIG. 11 is a set of electropherogram tracings showing the sequence results obtained from the protocol described in FIG. 9.

FIG. 10 is a summary of results obtained in an MJR thermocycler comparing enrichment of samples with different mutation load (mutation load in the initial samples is shown in the third column) of EGFR Exon 20 T790M by Step-up Fast COLD PCR and Fast COLD PCR at a fixed denaturation temperature. Samples were amplified in the presence or absence of serum DNA. The thermal cycler wells used are listed in the second column. The fold enrichment achieved in each well by Step-up Fast COLD PCR is shown in the fourth column from the left. The fold enrichment in each well achieved by Fast COLD PCR with the denaturing temperature set at 85.1° C. ($T_c$–0.5° C.) and 85.6° C. ($T_c$) are shown in the columns on the right. An example of sequencing using a reverse sequencing primer (5'-TGGCTCCTTATCTC-CCCTCC-3' (SEQ ID NO: 5) of the mixtures after the step-up PCR protocol described above in which the indicated amount of the target sequence was added is shown in FIG. 11. The limit of detection was 0.5% of the target sequence in the reference sequence.

Example 4

ICE COLD PCR for Determination of Presence of EGFR Exon 21 L858R Mutation

Figure 12:
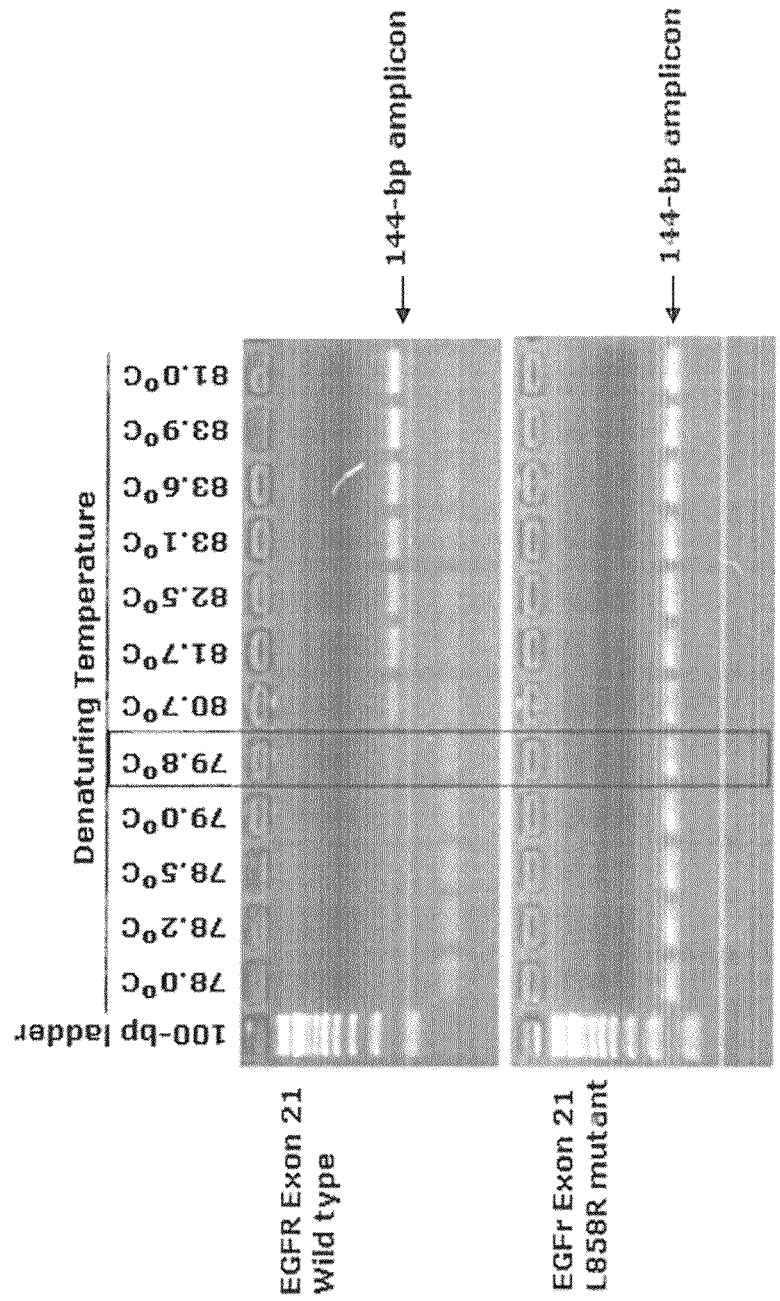
FIG. 12 is a photograph of a gel after a PCR reaction to determine the Tc for an ICE COLD PCR reaction for detection of EGFR Exon 21 L858R.

The first step was to determine the Critical Temperature ($T_c$) to enrich an EGFR Exon 21 L858R 144-bp amplicon. PCR was carried out with Taq DNA polymerase, Forward primer 5'GAACGTACTGGTGAAAACAC3'(SEQ ID NO: 6) and reverse primer 5'GTGTCAGGAAAATGCTG3' (SEQ ID NO: 7) and RS oligonucleotide containing 4 LNAs 5'GCT-GTATCGTCAAGGCACTCTTGCCTACG+C+CA+C+CAGCTCCAACTACCAC3' ((SEQ ID NO: 8) LNAs are indicated with a+ to the left of the nucleotide). PCR amplification was carried out in an MJ Gradient thermocycler and consisted of an initial denaturation at 95° C. for 2 minutes, followed by 5 cycles of standard PCR amplification with denaturation at 95° C. for 15 seconds, annealing at 61° C. for 15 seconds and extension at 72° C. for 30 seconds, followed by 40 cycles of ICE COLD-PCR with denaturation at the temperatures indicated in FIG. 12 for 10 seconds, annealing at 55° C. for 30 seconds and extension at 72° C. for 30 seconds. Empirical $T_c$ is shown in a rectangle in FIG. 12 and is 79.8° C.

ICE COLD PCR was then carried out using the traditional ICE COLD method at two different $T_c$s ($T_d$) or using the step-up methods described herein as shown in the Table in FIG. 13. The PCR was carried out on a thermal cycler using the calculated mode for the traditional ICE COLD PCR methods and in the block mode for the step-up methods of PCR. FIG. 14 is a summary of the results in an MJR thermal cycler comparing enrichment of samples with different mutation load (mutation load in the initial samples is shown in the third column) of EGFR Exon 21 L858R by Step-up ICE COLD PCR and ICE COLD PCR. Samples were amplified in the presence or absence of serum DNA. The thermal cycler wells used are listed in the second column. The fold enrichment achieved in each well by Step-up ICE COLD PCR is shown in the fourth column from the left. The fold enrichment in each well achieved by ICE COLD PCR with the denaturing temperature set at 78.6° C. ($T_c$–1.2° C.) and 79.8° C. ($T_c$) are shown in the columns on the right.

The PCR products were sequenced using a reverse sequencing primer (5'-GAAAATGCTGGCTGACCTA-3' (SEQ ID NO: 9)) after the step-up PCR protocol described above in which the indicated amount of the target sequence was added. The fold enrichment of the L858R mutation is reported in FIG. 14 and could be detected when 1% of the target sequence was included in the initial reaction mixture.

Example 5

ICE COLD PCR for determination of presence of EGFR Exon 19 ΔE746 mutation

An ICE COLD PCR method for the EGFR Exon 19 ΔE746 mutation was developed. The primers for use in this reaction were as follows: forward primer: 5'-AGTTAAAATTC-CCGTCGCTAT-3' (SEQ ID NO: 10) and reverse primer: 5'-TTCAGAGCCATGGACCC-3' (SEQ ID NO: 11). In FIG. 15, the conditions for the ICE COLD PCR protocols at a fixed temperature are shown on the left and a Step-up ICE COLD PCR protocol is shown on the right. Fixed temperature protocols were carried out in the thermocycler Calculated Mode, while the Step-up ICE COLD PCR protocol was carried out in the Block Mode. The $T_c$ for EGFR Exon 19 in the experimental conditions used was 73.8° C.

FIG. 16 shows a summary of results in an MJR thermal cycler comparing enrichment of samples with different mutation load (mutation load in the initial samples is shown in the third column) of EGFR Exon 19 ΔE746 bp Step-up ICE COLD PCR and ICE COLD PCR at a fixed denaturation temperature. Samples were amplified in the presence or absence of serum DNA. The thermal cycler wells used are listed in the second column. The fold enrichment achieved in each well by Step-up ICE COLD PCR is shown in the fourth column from the left. The fold enrichment in each well achieved by ICE COLD PCR with the denaturing temperature set at 73.8° C. ($T_c$) and 74.8° C. ($T_c$+1° C.) are shown in the columns on the right.

I claim:

1. A step-up method for enriching a target sequence in an amplification reaction mixture, said method comprising:
   a) preparing an amplification reaction mixture including at least the following constituents:
   a primer pair capable of amplifying a reference sequence and a nucleic acid sample having the reference sequence and also suspected of having one or more target sequences that are at least 50% homologous to said reference sequence and are also amplifiable by the same primer pair as said reference sequence, and a molar excess of a reference blocking sequence relative to the amount of reference sequence, the reference blocking sequence is fully complementary with at least a portion of the sequence of one of the strands of the reference sequence between or overlapping its primer binding sites, and wherein the target sequence is less prevalent than the reference sequence;
   b) selecting a critical temperature ($T_c$) sufficient to permit preferential denaturation of heteroduplexes of the reference blocking sequence and target strands as compared to denaturation duplexes of the reference blocking sequence and reference strands;
   c) selecting second denaturing temperatures ($T_{d2}$) for multiple sets of amplification cycles the second denaturing temperature ($T_{d2}$) for a first set of amplification cycles being less than the selected critical temperature ($T_c$) and the second denaturing temperature ($T_{d2}$) for subsequent sets of amplification cycles being progressively higher than the previous set of amplification cycles;
   d) for each set of amplification cycles, cycling through the following steps to enrich the target sequence in the amplification reaction mixture:
   1) increasing the temperature of the amplification reaction mixture to a first denaturing temperature ($T_{d1}$) that is above the melting temperature ($T_m$) of the double-stranded reference sequence and above the melting temperature ($T_m$) of the double-stranded target sequence to form reference strands and target strands;
   2) reducing the temperature of the amplification reaction mixture to permit formation of duplexes of the reference blocking sequence and the complementary reference strand and heteroduplexes of the reference blocking sequence and the target strands;
   3) increasing the temperature of the amplification reaction mixture to the selected second denaturing temperature ($T_{d2}$);
   4) reducing the temperature of the amplification reaction mixture to permit said primer pair to anneal to target strands and reference strands in the amplification reaction mixture; and
   5) extending said primers annealed to the free target strands and free reference strands in the reaction mixture to enrich said target sequence relative to said reference sequence; and
   e) repeating step (d) for each set of amplification cycles using said selected second denaturing temperatures ($T_{d2}$) for the respective set of amplification cycles.

2. The method of claim 1, wherein a 3' end on the reference blocking sequence is blocked to inhibit extension.

3. The method of claim 1, wherein the 5' end on the reference blocking sequence comprises a nucleotide that prevents 5' to 3' exonucleolysis by Taq DNA polymerases.

4. The method of claim 1, wherein the reference blocking sequence is one of single stranded DNA, RNA, peptide nucleic acid, locked nucleic acid or a modified nucleic acid.

5. The method of claim 1, wherein the reference blocking sequence is a chimera between single stranded DNA, RNA, peptide nucleic acid, locked nucleic acid or another modified nucleotide.

6. The method of claim 5, wherein the position of the peptide nucleic acid or locked nucleic acid on the chimera sequence is selected to match at least one position where a mutation is suspected to be present, thereby maximizing the difference between the temperature needed to denature heteroduplexes of the reference blocking sequence and target strands and the temperature needed to denature heteroduplexes of the reference blocking sequence and the complementary reference strand.

7. The method of claim 1, wherein the reference blocking sequence is fully complementary with one of the strands of the reference sequence between its primer binding sites, or overlapping at either of the primer binding sites.

8. The method of claim 1, wherein the reference blocking sequence is added to the amplification reaction mixture at a concentration of at least 25 nM.

9. The method of claim 1, wherein step (d)(2) is held for less than one minute.

10. The method of claim 1, further comprising repeating steps (d)(2) and (d)(3) more than one time.

11. The method of claim 1, wherein the second denaturing temperature ($T_{d2}$) is adjusted in equal temperature increments between each set of amplification cycles.

12. The method of claim 1, wherein the second denaturing temperature ($T_{d2}$) is defined by the following equation: $T_{d2} = T_{d2i} + k\Delta$ where $T_{d2i}$ is the second denaturing temperature selected for the initial set of amplification cycles; $\Delta$ is a fixed temperature increment between sets of amplification cycles; k is an index indicating the respective cycle set (k=1, 2, 3 . . . K), and K represents the total number of cycle sets.

13. The method of claim 12, wherein the second denaturing temperature ($T_{d2}$) for the final set of amplification cycles is greater than or equal to the selected critical ($T_c$).

14. The method of claim 12, wherein the second denaturing temperature selected for the initial set of amplification cycles ($T_{d2i}$) is at least 0.5° centigrade less than the selected critical temperature ($T_c$).

15. The method of claim 14, wherein the fixed temperature increment between sets of amplification cycles $\Delta$ is selected to be at least 0.1° centigrade and K is equal to or greater than 4.

16. The method of claim 1, wherein said target and reference sequences are first amplified by subjecting the nucleic acid sample to PCR using the first denaturing temperature ($T_{d1}$) that is higher than the melting temperature ($T_m$) of said reference sequence prior to use in the method.

17. The method of claim 1 wherein the method is implemented in multiple PCR reaction tubes placed in a thermocycler and said thermocycler is operated in block mode.

18. The method of claim 1, wherein said target sequence is differentially methylated from the reference sequence and the nucleic acid sample is optionally treated with sodium bisulfite prior to implementing the method of any one of the preceding claims on the reaction mixture.

19. The method of claim 1, wherein after enrichment the reaction mixture with enriched target sequence is analyzed using one or more of the methods selected from the group consisting of: matrix assisted laser/desorption ionization time-of-flight (MALDI-TOF), high resolution (HR)-melting, Di-deoxy-sequencing, Single-molecule sequencing, pyrosequencing, Second generation high-throughput sequencing, single strand conformation polymorphism (SSCP), restriction fragment length polymorphism (RFLP), denaturing high pressure liquid chromatography (dHPLC), chemical cleavage of mismatch (CCM), digital PCR and quantitative-PCR.

20. The method of claim 1, wherein said target sequence is a mutant allele comprising one or more deletions, insertions or alterations.

21. The method of claim 1, wherein said reaction mixture contains a nucleic acid detection dye or a labeled probe.

22. The method of claim 21, wherein said method is performed in a real-time PCR device.

23. The method of claim 1, wherein each set of amplification cycles includes 3-20 cycles.

24. The method of claim 1, wherein said method is used to enrich two or more different target sequences and said method further comprises one or more additional pairs of primers specific to said target sequences.

25. The method of claim 1, wherein said primer pair has a melting temperature that is below the $T_c$.

26. The method of claim 1, wherein the amplification reaction mixture includes a modified nucleic acid.

27. A step-up method for enriching a target sequence in an amplification reaction mixture, said method comprising:
  a) preparing an amplification reaction mixture including at least the following constituents:
    a primer pair capable of amplifying a reference sequence and a nucleic acid sample having the reference sequence and also suspected of having one or more target sequences that are at least 50%, homologous to said reference sequence and are also amplifiable by the same primer pair as said reference sequence and
    wherein the target sequence is less prevalent than the reference sequence;
  b) selecting a critical temperature ($T_c$) sufficient to permit preferential denaturation of heteroduplexes of a strand of the reference sequence and a strand of the target sequence yet insufficient to denature homoduplexes of the reference sequence;
  c) selecting second denaturing temperatures ($T_{d2}$) for multiple sets of amplification cycles, the second denaturing temperature ($T_{d2}$) for a first set of amplification cycles being less than the selected critical temperature ($T_c$) and the second denaturing temperature ($T_{d2}$) for subsequent sets of amplification cycles being progressively higher than the previous set of amplification cycles;
  d) for each set of amplification cycles, cycling through the following steps to enrich the target sequence in the amplification reaction mixture:
    1) subjecting the amplification reaction mixture to a first denaturing temperature ($T_{d1}$) that is above the melting temperature ($T_m$) of the reference sequence and the target sequence to form reference strands and target strands;
    2) reducing the temperature of the amplification reaction mixture to permit formation of heteroduplexes of the reference strands and the target strands of step (1);
    3) increasing the temperature of the amplification reaction mixture to the selected second denaturing temperature ($T_{d2}$);
    4) reducing the temperature of the amplification reaction mixture to permit said primer pair to anneal to target strands and reference strands in the amplification reaction mixture; and
    5) extending said primer pair to enrich said target sequence relative to said reference sequence; and
  e) repeating step (d) for each set of amplification cycles using said selected second denaturing temperatures ($T_{d2}$) for the respective set of amplification cycles.

28. A step-up method for enriching a target nucleic acid sequence in an amplification reaction mixture, said method comprising:
  a) preparing an amplification reaction mixture having a nucleic acid sample having a reference sequence and suspected of having a target sequence that is at least 50% homologous to the reference sequence, has a melting temperature ($T_m$) below the melting temperature ($T_m$) of said reference sequence and is amplifiable by the same primer pair as said reference sequence;
  b) selecting a critical temperature ($T_c$) sufficient to permit preferential denaturation of said target sequence yet insufficient to substantially denature said reference sequence;
  c) selecting second denaturing temperatures ($T_{d2}$) for multiple sets of amplification enrichment cycles, the second denaturing temperature ($T_{d2}$) for a first set of one or more amplification enrichment cycles being less than the critical temperature ($T_c$) and the second denaturing temperature ($T_{d2}$) for subsequent sets of amplification enrichment cycles being progressively higher than the previous set of amplification enrichment cycles;
  d) for multiple sets of amplification enrichment cycles, cycling through the following steps in order to enrich the target sequence in the amplification reaction mixture:
    1) subjecting the amplification reaction mixture suspected of having said target sequence to the selected second denaturing temperature ($T_{d2}$);
    2) reducing the temperature of the reaction mixture so as to allow a primer pair to anneal to said target sequence; and
    3) extending said primer pair so as to enrich said target sequence relative to said reference sequence in the reaction mixture; and
  e) repeating step d for each set of amplification enrichment cycles using said second denaturing temperature ($T_{d2}$) for the respective set of amplification enrichment cycles.

* * * * *